(12) United States Patent
Tanabe et al.

(10) Patent No.: US 11,166,687 B2
(45) Date of Patent: Nov. 9, 2021

(54) X-RAY IMAGING APPARATUS

(71) Applicant: Shimadzu Corporation, Kyoto (JP)

(72) Inventors: Koichi Tanabe, Kyoto (JP); Yukihisa Wada, Kyoto (JP); Satoshi Tokuda, Kyoto (JP); Satoshi Sano, Kyoto (JP); Akira Horiba, Kyoto (JP)

(73) Assignee: Shimadzu Corporation, Kyoto (JP)

(*) Notice: Subject to any disclaimer, the term of this patent is extended or adjusted under 35 U.S.C. 154(b) by 20 days.

(21) Appl. No.: 16/955,312

(22) PCT Filed: Nov. 8, 2018

(86) PCT No.: PCT/JP2018/041496
§ 371 (c)(1),
(2) Date: Jun. 18, 2020

(87) PCT Pub. No.: WO2019/130848
PCT Pub. Date: Jul. 4, 2019

(65) Prior Publication Data
US 2021/0015437 A1    Jan. 21, 2021

(30) Foreign Application Priority Data
Dec. 26, 2017  (JP) .............................. JP2017-249880

(51) Int. Cl.
*A61B 6/00* (2006.01)
*A61B 6/10* (2006.01)

(52) U.S. Cl.
CPC .............. *A61B 6/484* (2013.01); *A61B 6/107* (2013.01); *A61B 6/4035* (2013.01); *A61B 6/5211* (2013.01); *A61B 6/5282* (2013.01)

(58) Field of Classification Search
CPC ............ G01N 23/041; G01N 2223/505; G01T 1/2006; G01T 1/2002; A61B 6/484;
(Continued)

(56) References Cited

U.S. PATENT DOCUMENTS

2012/0307966 A1  12/2012  Roessl et al.
2017/0343486 A1  11/2017  Tanabe et al.
2019/0159742 A1* 5/2019  Behling ................. A61B 6/484

FOREIGN PATENT DOCUMENTS

JP   2013-513414 A   4/2013
WO  2016/104008 A1  6/2016

OTHER PUBLICATIONS

International Search Report with English translation and Written Opinion with Machine translation dated Feb. 5, 2019 in corresponding International Application No. PCT/JP2018/041496; 9 pages.
(Continued)

*Primary Examiner* — Don K Wong
(74) *Attorney, Agent, or Firm* — Maier & Maier, PLLC

(57) ABSTRACT

In an X-ray imaging apparatus an image processor is configured to generate a phase contrast image based on a plurality of first images acquired by a first detection region (R1) at a plurality of relative positions of the first detection region with respect to a subject (T) to be imaged, and to generate an absorption image based on a plurality of second images acquired by a second detection region (R2) at a plurality of relative positions of the second detection region with respect to the subject.

19 Claims, 10 Drawing Sheets

(58) Field of Classification Search
CPC ..... A61B 6/584; A61B 6/4291; A61B 6/4021;
A61B 6/405; A61B 6/542; A61B 6/5294;
A61B 6/5258; A61B 6/488; A61B
6/4035; A61B 6/4233; A61B 6/502; A61B
6/06; A61B 6/025; A61B 6/5205; A61B
6/582; A61B 6/4241
See application file for complete search history.

(56) References Cited

OTHER PUBLICATIONS

Kai Scherer, et al., "Toward Clinically Compatible Phase-Contrast Mammography", PLOS ONE, US, PLOS, Jun. 25, 2015, DOI: 10.1371/journal.pone.0130776, 7 pgs.

* cited by examiner

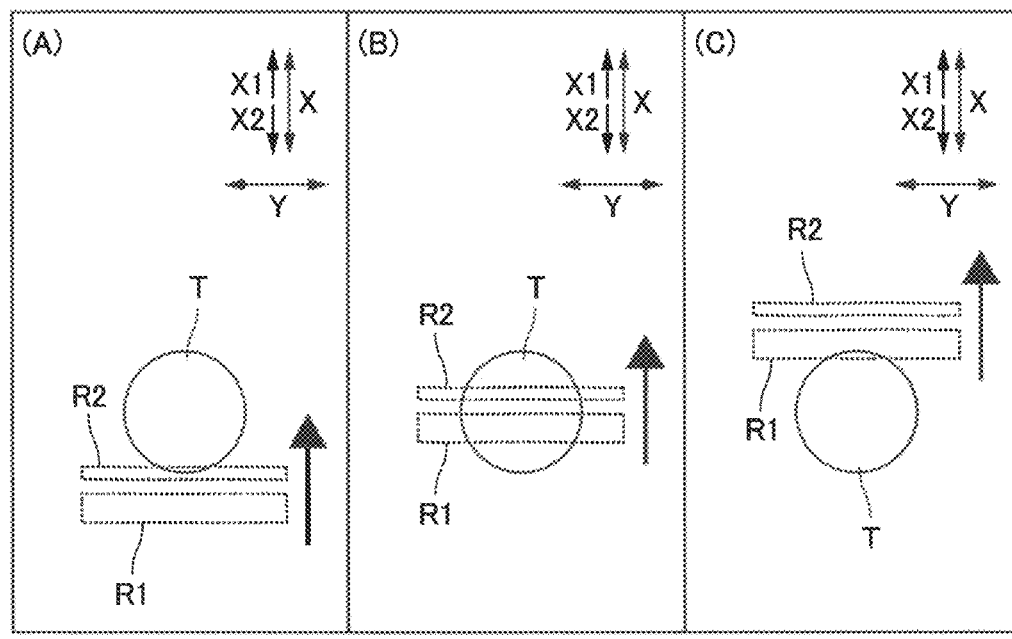
FIG. 3(A)   FIG. 3(B)   FIG. 3(C)
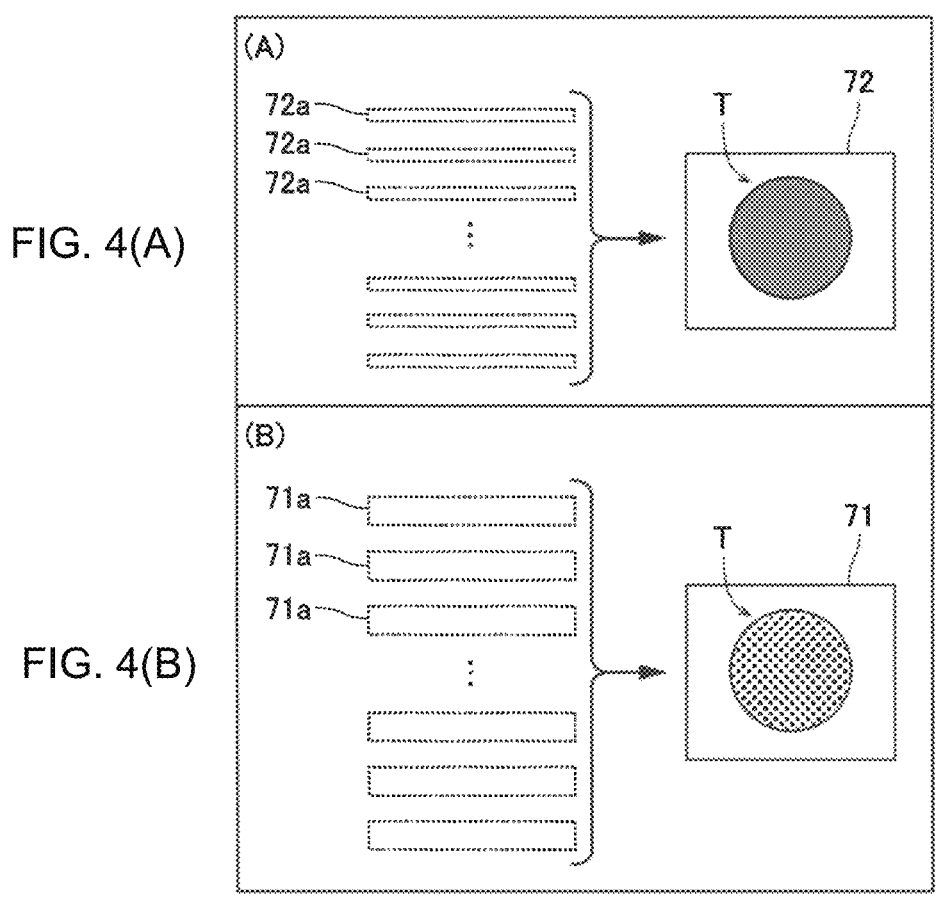
FIG. 4(A)
FIG. 4(B)

FIG.5 [FIRST MODIFIED EXAMPLE OF FIRST EMBODIMENT]
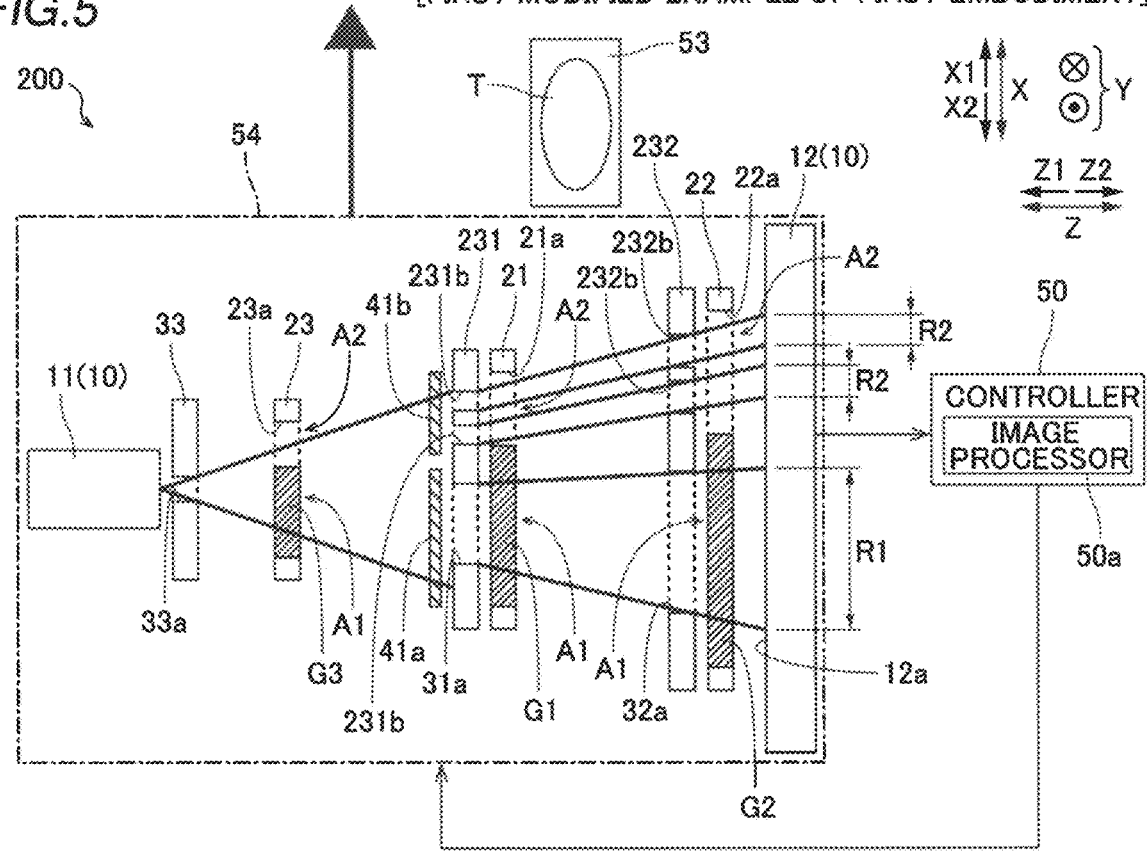
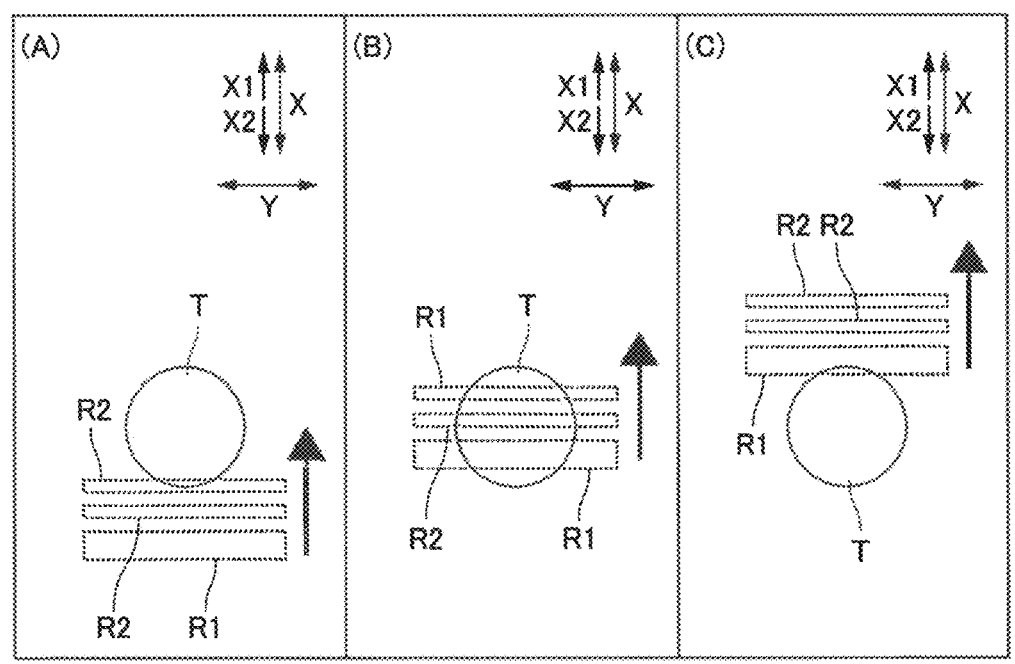
FIG. 6(A)  FIG. 6(B)  FIG. 6(C)

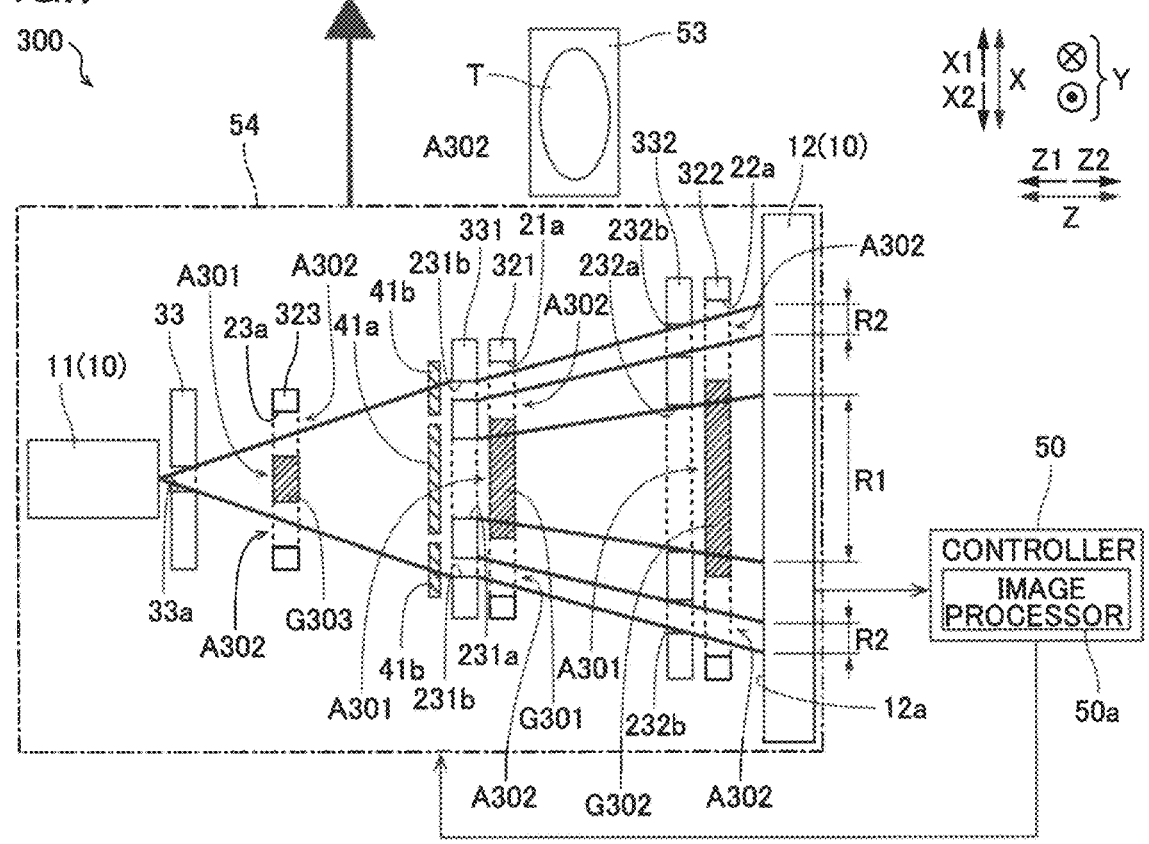
FIG. 7  [SECOND MODIFIED EXAMPLE OF FIRST EMBODIMENT]
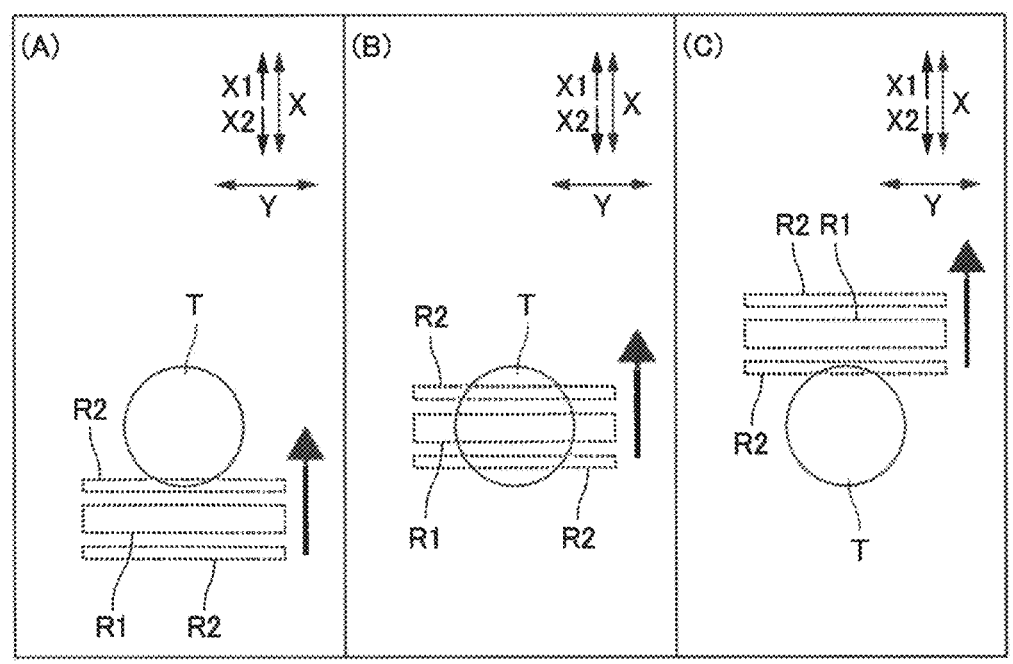
FIG. 8(A)   FIG. 8(B)   FIG. 8(C)

[MODIFIED EXAMPLE OF SECOND EMBODIMENT]

[ANOTHER MODIFIED EXAMPLE]

FIG. 15
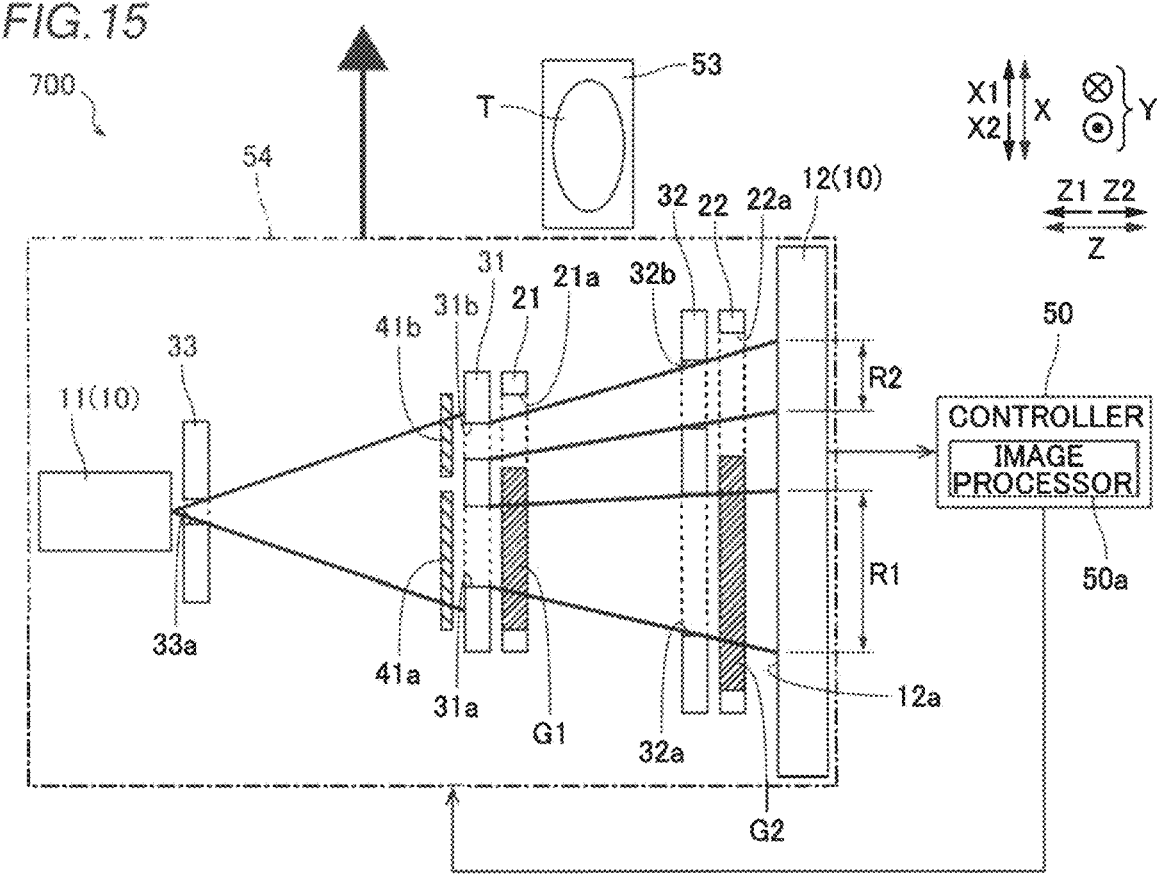
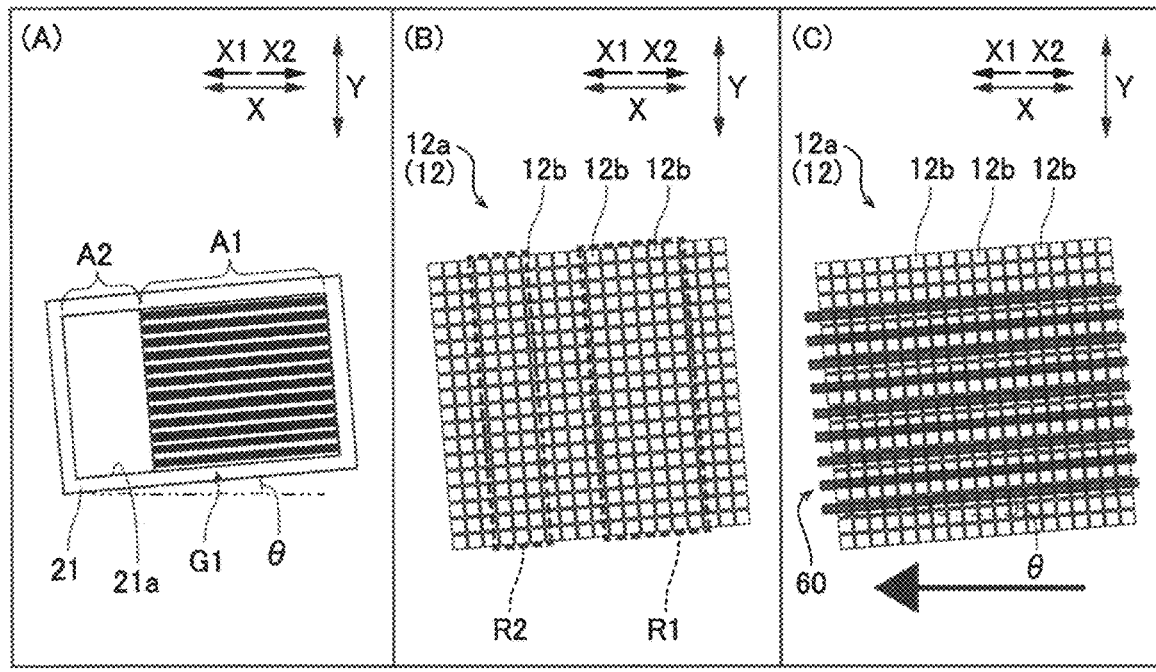
FIG. 16(A)   FIG. 16(B)   FIG. 16(C)

X-RAY IMAGING APPARATUS

TECHNICAL FIELD

The present invention relates to an X-ray imaging apparatus including a grating on which a grating pattern is formed so as to diffract or shield X-rays radiated from an X-ray source.

BACKGROUND ART

Conventionally, an X-ray imaging apparatus including a grating on which a grating pattern is formed so as to diffract X-rays radiated from an X-ray source is known. Such an X-ray imaging apparatus is disclosed in Kai Scherer, et al., "Toward Clinically Compatible Phase-Contrast Mammography", PLOS ONE, US, PLOS, Jun. 25, 2015, DOI: 10.1371/journal.pone.0130776, for example.

Kai Scherer, et al., "Toward Clinically Compatible Phase-Contrast Mammography", PLOS ONE, US, PLOS, Jun. 25, 2015, DOI: 10.1371/journal.pone.0130776 discloses a phase imaging device (X-ray imaging apparatus) including an X-ray source, a phase grating on which a grating pattern is formed so as to diffract X-rays radiated from the X-ray source, and a detector configured to detect the X-rays diffracted by the phase grating. The phase imaging device disclosed in Kai Scherer, et al., "Toward Clinically Compatible Phase-Contrast Mammography", PLOS ONE, US, PLOS, Jun. 25, 2015, DOI: 10.1371/journal.pone.0130776 is configured as a mammography apparatus configured to image a breast. A technique in which in addition to the phase grating that diffracts the X-rays, a grating for interfering with a self-image generated by the phase grating is provided, a technique in which a self-image is directly detected using a fine pixel detector, or a technique in which a scintillator (a substance for detecting X-rays) is formed in a grid shape to interfere with a self-image is used to detect X-rays diffracted by a phase grating.

PRIOR ART

Non-Patent Document

Non-Patent Document 1: Kai Scherer, et al., "Toward Clinically Compatible Phase-Contrast Mammography", PLOS ONE, US, PLOS, Jun. 25, 2015, DOI: 10.1371/journal.pone.0130776

SUMMARY OF THE INVENTION

Problems to be Solved by the Invention

In X-ray phase imaging using an X-ray imaging apparatus as disclosed in Kai Scherer, et al., "Toward Clinically Compatible Phase-Contrast Mammography", PLOS ONE, US, PLOS, Jun. 25, 2015, DOI: 10.1371/journal.pone.0130776, in addition to an absorption image obtained by normal X-ray imaging without using a phase grating, a phase differential image (refracted image) and a dark-field image (scattering image) are generated. Of these images, for example, in the diagnosis of breast cancer, faint shadows and shapes in the absorption image are interpreted such that it is determined whether a tumor is benign or malignant. Furthermore, it is known that the dark-field image is excellent in depiction of tissue calcification (calcium deposition) caused by breast cancer and depiction of cancer boundaries. Therefore, the X-ray imaging apparatus (mammography apparatus) as disclosed in Kai Scherer, et al., "Toward Clinically Compatible Phase-Contrast Mammography", PLOS ONE, US, PLOS, Jun. 25, 2015, DOI: 10.1371/journal.pone.0130776 is used such that it is possible to diagnose breast cancer in combination of an absorption image for determining whether a tumor is benign or malignant and a dark-field image that is excellent in depiction of calcification and cancer boundaries.

However, the absorption image generated by the X-ray phase imaging using the X-ray imaging apparatus as disclosed in Kai Scherer, et al., "Toward Clinically Compatible Phase-Contrast Mammography", PLOS ONE, US, PLOS, Jun. 25, 2015, DOI: 10.1371/journal.pone.0130776 has a problem that the contrast is inferior due to detecting X-rays that have passed through a phase grating as compared with the absorption image generated by the normal X-ray imaging in which X-rays that do not pass through a phase grating are detected. Therefore, in order to generate an absorption image for diagnosis, it is necessary to perform the normal X-ray imaging using an ordinary X-ray imaging apparatus separately from the X-ray phase imaging by the X-ray imaging apparatus as disclosed in Kai Scherer, et al., "Toward Clinically Compatible Phase-Contrast Mammography", PLOS ONE, US, PLOS, Jun. 25, 2015, DOI: 10.1371/journal.pone.0130776. However, the normal X-ray imaging and the X-ray phase imaging are performed by the separate apparatuses, and thus there is a problem that a position at which a subject is imaged in the normal X-ray imaging and a position at which the subject is imaged in the X-ray phase imaging are not matched. In addition to the diagnosis of breast cancer, in the case of diagnosis in another medical examination or evaluation in non-destructive inspection, for example, the same problem as described above conceivably occurs when an absorption image, a phase differential image, and a dark-field image are combined.

The present invention is intended to solve the above problems. The present invention aims to provide an X-ray imaging apparatus capable of significantly reducing or preventing a decrease in the accuracy of diagnosis (evaluation) based on images captured by normal X-ray imaging and X-ray phase imaging.

Means for Solving the Problems

In order to attain the aforementioned object, an X-ray imaging apparatus according to an aspect of the present invention includes an X-ray source, a first grating having a grating pattern formed to diffract or shield X-rays radiated from the X-ray source, a detector including a first detection region configured to detect the X-rays that have passed through the first grating and have reached the first detection region, and a second detection region configured to detect the X-rays that have reached the second detection region without passing through the first grating, a relative position changer configured to change relative positions of the first detection region and the second detection region with respect to a subject to be imaged, and an image processor configured to generate a phase or scattering contrast image based on a plurality of first images acquired by the first detection region at a plurality of relative positions of the first detection region with respect to the subject, and to generate an absorption image based on a plurality of second images acquired by the second detection region at a plurality of relative positions of the second detection region with respect to the subject.

In the X-ray imaging apparatus according to this aspect of the present invention, as described above, the image processor is configured to generate the phase or scattering contrast image based on the plurality of first images acquired by the first detection region at the plurality of relative positions of the first detection region with respect to the subject, and to generate the absorption image based on the plurality of second images acquired by the second detection region at the plurality of relative positions of the second detection region with respect to the subject. Accordingly, the phase or scattering contrast image and the absorption image can be generated based on the first images and the second images acquired at the same time, and thus the imaging position of the subject for each image in normal X-ray imaging and the imaging position of the subject for each image in X-ray phase imaging can be easily matched. Consequently, as compared with the case in which the normal X-ray imaging and the X-ray phase imaging are performed by separate apparatuses, it is possible to easily match the imaging positions of the subject for each image, and thus a decrease in the accuracy of diagnosis (evaluation) based on the images captured by the normal X-ray imaging and the X-ray phase imaging can be significantly reduced or prevented. Accordingly, in diagnosis in a medical examination, evaluation in non-destructive inspection, etc., when the same subject has a portion that is likely to be depicted in only one of the absorption image and phase differential and dark-field images and a portion that is likely to be depicted in only the other of the absorption image and the phase differential and dark-field images, the diagnosis (evaluation) can be performed with high accuracy.

In the aforementioned X-ray imaging apparatus according to this aspect, the image processor is preferably configured to generate a dark-field image based on the plurality of first images acquired by the first detection region at the plurality of relative positions of the first detection region with respect to the subject, and to generate the absorption image based on the plurality of second images acquired by the second detection region at the plurality of relative positions of the second detection region with respect to the subject. Accordingly, the absorption image generated by the normal X-ray imaging and the dark-field image generated by the X-ray phase imaging can be easily generated in a state in which the imaging positions of the subject are matched. Consequently, it is possible to significantly reduce or prevent a decrease in the accuracy of the diagnosis (evaluation) based on the absorption image generated by the normal X-ray imaging and the dark-field image generated by the X-ray phase imaging. Thus, for example, in the diagnosis of breast cancer, the absorption image for determining whether a tumor is benign or malignant and the dark-field image that is excellent in depiction of calcification and cancer boundaries are combined such that the diagnosis is performed with high accuracy.

In the aforementioned X-ray imaging apparatus according to this aspect, the relative position changer preferably includes a moving mechanism configured to change the relative positions of the first detection region and the second detection region with respect to the subject by moving an imager including the X-ray source and the detector and the first grating with respect to the subject, moving the subject with respect to the imager and the first grating, or moving the first grating with respect to the subject and the imager. Accordingly, the relative positions of the first detection region and the second detection region with respect to the subject can be easily changed by the moving mechanism.

In this case, the moving mechanism is preferably configured to continuously change relative positions of the imager and the first grating with respect to the subject in a predetermined direction by continuously moving either the imager and the first grating or the subject in the predetermined direction in a state in which a relative position of the first grating with respect to the imager is maintained, and the image processor is preferably configured to generate the phase or scattering contrast image and the absorption image based on the plurality of first images and the plurality of second images, respectively, generated by continuous changes of the relative positions of the imager and the first grating with respect to the subject by the moving mechanism. Accordingly, the plurality of first images and the plurality of second images aligned in the predetermined direction can be acquired by continuously changing the relative positions of the imager and the first grating with respect to the subject in the predetermined direction. Consequently, a large-area phase or scattering contrast image and a large-area absorption image can be easily generated based on the plurality of first images and the plurality of second images aligned in the predetermined direction, respectively. Furthermore, the phase or scattering contrast image can be generated simply by continuously changing the relative positions of the imager and the first grating with respect to the subject in the predetermined direction, and thus the X-ray phase imaging can be performed without precise adjustment of the positional relationship between the imager and the first grating for forming the self-image by the first grating.

In the aforementioned configuration in which the moving mechanism continuously changes the relative positions of the imager and the first grating with respect to the subject, the first detection region and the second detection region are preferably aligned along a direction in which the relative positions of the imager and the first grating with respect to the subject are continuously changed, and the moving mechanism is preferably configured to change the relative positions in such a manner that the detector detects the X-rays from a side of the second detection region among the first detection region and the second detection region. Accordingly, acquisition of the second images in the second detection region can be started before acquisition of the first images in the first detection region, and thus it is possible to determine, based on the absorption image based on the second images captured halfway, whether or not it is necessary to generate the phase or scattering contrast image based on the first images acquired after the second images. Consequently, when it is determined from a part of the absorption image that the phase or scattering contrast image is unnecessary, only the normal X-ray imaging for generating the absorption image is performed continuously, and the X-ray phase imaging for generating the phase or scattering contrast image is not performed such that unnecessary X-ray radiation to the subject can be significantly reduced or prevented. Thus, in the diagnosis in a medical examination, for example, it is possible to significantly reduce or prevent an increase in the X-ray dose to which a patient is exposed.

The aforementioned configuration in which the moving mechanism continuously changes the relative positions of the imager and the first grating with respect to the subject preferably further includes an irradiation range adjustment member arranged on a side of the X-ray source with respect to the subject between the X-ray source and the first grating, the irradiation range adjustment member including a first irradiation range adjuster configured to adjust an irradiation range of the X-rays reaching the first detection region and a second irradiation range adjuster configured to adjust an irradiation range of the X-rays reaching the second detection region. Accordingly, the first irradiation range adjuster and the second irradiation range adjuster can easily adjust the irradiation range of the X-rays reaching the first detection region and the second detection region, respectively. Consequently, the total amounts of X-rays that respectively reach the first detection region and the second detection region can be easily adjusted so as to be optimum amounts for generating the phase or scattering contrast image and the absorption image.

In this case, the first irradiation range adjuster and the second irradiation range adjuster are preferably arranged apart from each other along a direction in which the relative positions of the imager and the first grating with respect to the subject are continuously changed. Accordingly, the first irradiation range adjuster and the second irradiation range adjuster are arranged apart from each other, and thus as compared with the case in which the first irradiation range adjuster and the second irradiation range adjuster are not arranged apart from each other, adjustment of the X-ray irradiation range by the first irradiation range adjuster and adjustment of the X-ray irradiation range by the second irradiation range adjuster can be easily and independently performed. Furthermore, the first irradiation range adjuster and the second irradiation range adjuster are arranged apart from each other along the direction in which the relative positions of the imager and the first grating with respect to the subject are continuously changed, and thus the time for determining, based on the absorption image based on the second images captured halfway, whether or not it is necessary to generate the phase or scattering contrast image based on the first images acquired after the second images can be easily ensured.

In the aforementioned configuration including the irradiation range adjustment member, the irradiation range of the X-rays reaching the second detection region adjusted by the second irradiation range adjuster is preferably smaller than the irradiation range of the X-rays reaching the first detection region adjusted by the first irradiation range adjuster. When images with substantially the same resolution are generated, the amount of X-rays required to generate the absorption image based on the second images is smaller than the amount of X-rays required to generate the phase or scattering contrast image based on the first images. Therefore, with the aforementioned configuration, the amount of X-rays reaching the second detection region can be smaller than the amount of X-rays reaching the first detection region, and thus when both the phase or scattering contrast image based on the first images and the absorption image based on the second images are generated, it is possible to significantly reduce or prevent radiation, to the subject, of X-rays other than those necessary for image generation.

In the aforementioned configuration including the irradiation range adjustment member, at least the second irradiation range adjuster of the first irradiation range adjuster and the second irradiation range adjuster preferably includes a plurality of second irradiation range adjusters, and the plurality of second irradiation range adjusters are preferably configured to adjust the irradiation range of the X-rays reaching the second detection region by changing a number of the second irradiation range adjusters that transmit the X-rays. Accordingly, the second irradiation range adjuster can easily adjust the amount of X-rays reaching the second detection region without passing through the grating in order to generate the absorption image. Consequently, when there is a difference in the amount of X-rays necessary for generating the absorption image due to a difference in a subject to be imaged, the amount of X-rays used to generate the absorption image after reaching the second detection region can be easily adjusted to an optimum amount of X-rays for each subject to be imaged.

The aforementioned configuration in which the moving mechanism continuously changes the relative positions of the imager and the first grating with respect to the subject preferably further includes a first filter arranged on a side of the X-ray source with respect to the subject and configured to adjust a spectrum of the X-rays radiated to the first detection region, and a second filter arranged on the side of the X-ray source with respect to the subject and configured to adjust a spectrum of the X-rays reaching the second detection region. Accordingly, regardless of the spectrum of the X-rays radiated from the X-ray source, the spectrum of the X-rays reaching the first detection region and the second detection region can be easily adjusted individually to the spectrum of X-rays suitable for generating the phase or scattering contrast image based on the first images and the absorption image based on the second images.

The aforementioned X-ray imaging apparatus according to this aspect preferably further includes an adjustment mechanism configured to adjust a relative position between the first grating and the first filter and a relative position between the first grating and the second filter. Accordingly, the relative positions of the first filter and the second filter with respect to the first grating can be adjusted such that the spectrum of the X-rays radiated from the X-ray source is appropriately filtered.

In the aforementioned configuration in which the relative position changer includes the moving mechanism, the moving mechanism is preferably configured to change the relative positions of the first detection region and the second detection region with respect to the subject by moving the first grating with respect to the subject and the imager, and the imager is preferably configured to perform imaging a plurality of times, and generate the first images and the second images in a state in which the relative positions of the first detection region and the second detection region with respect to the subject are changed by the moving mechanism such that the relative positions are different in each imaging. Accordingly, the plurality of first images and the plurality of second images acquired by performing imaging a plurality of times and for which the relative positions are different can be acquired. Consequently, a large-area phase or scattering contrast image and a large-area absorption image can be easily generated based on the plurality of first images and the plurality of second images for which the relative positions are different, respectively. In addition, the region of the detector necessary for generating the phase or scattering contrast image or the absorption image can be matched with the sum of the first detection region and the second detection region, and thus a distance in which the first grating is moved can be decreased as compared with the case in which the first grating is completely retracted from the X-ray irradiation range in order to perform the normal X-ray imaging separately from the X-ray phase imaging, for example. Consequently, it is possible to significantly reduce or prevent an increase in the total imaging time for performing the normal X-ray imaging and the X-ray phase imaging.

In this case, the first detection region and the second detection region, respectively, preferably include a plurality of first detection regions and a plurality of second detection regions, and are preferably alternately arranged. Accordingly, the first detection regions and the second detection regions are alternately arranged, and thus the positions of the first detection regions and the positions of the second detection regions at the second imaging are reversed from those at the first imaging such that it is possible to generate the phase or scattering contrast image and the absorption image respectively having sizes of imaging ranges obtained by combining the first images acquired by the first detection regions with the second images acquired by the second detection regions by performing imaging only twice. Furthermore, the plurality of first detection regions and the plurality of second detection regions are provided, and thus a distance in which each first grating is moved at the first imaging and the second imaging can be decreased as compared with the case in which a plurality of first gratings are not provided. Consequently, it is possible to reliably significantly reduce or prevent an increase in the total imaging time for performing the normal X-ray imaging and the X-ray phase imaging.

The aforementioned configuration in which the moving mechanism changes the relative positions of the first detection region and the second detection region with respect to the subject by moving the first grating with respect to the subject and the imager preferably further includes an anti-scatter member arranged at a position corresponding to the second detection region among the first detection region and the second detection region and configured to remove scattered rays. Accordingly, it is possible to significantly reduce or prevent the scattered rays other than the X-rays radiated from the X-ray source and reaching the second detection region without passing through the first grating from reaching the second detection region. Consequently, it is possible to significantly reduce or prevent generation of noise in the absorption image due to the influence of the scattered rays.

In the aforementioned configuration in which the relative position changer includes the moving mechanism configured to change the relative positions of the first detection region and the second detection region with respect to the subject, a distance of the second detection region from the subject is preferably smaller than a distance of the first detection region from the subject. In the absorption image, as the distance from the subject to the detector increases, a portion of the subject's penumbra (image blurring) caused by the focal point size of the X-ray source increases. Therefore, with the aforementioned configuration, it is possible to significantly reduce or prevent an increase in the image blurring generated in the absorption image detected in the second detection region.

In the aforementioned configuration in which the relative position changer includes the moving mechanism configured to change the relative positions of the first detection region and the second detection region with respect to the subject, imaging is preferably performed a plurality of times so as to change an angle of incidence of the X-rays on the subject, and the first images and the second images are generated in the first detection region and the second detection region in each imaging in which the angle of incidence is changed, and the image processor is preferably configured to select the first images and the second images having same angles of incidence of the X-rays on the subject, and to generate the phase or scattering contrast image and the absorption image based on the first images and second images that have been selected. Accordingly, the phase or scattering contrast image and the absorption image having the same angles of incidence of the X-rays on the subject can be generated, and thus the phase or scattering contrast image and the absorption image can be accurately compared even when the subject is thick.

The aforementioned X-ray imaging apparatus according to this aspect preferably further includes a second grating arranged between the first grating and the detector and configured to interfere with a self-image of the first grating. Accordingly, the self-image of the first grating interferes with the second grating such that interference fringes having a pitch larger than that of the self-image of the first grating can be formed. Consequently, the formed interference fringes are detected such that as compared with the case in which the self-image of the first grating is directly detected, an increase in the detection accuracy of the detector required for the phase or scattering contrast image can be significantly reduced or prevented.

In the aforementioned X-ray imaging apparatus according to this aspect, a resolution of an image to be detected by the first detection region is preferably different from a resolution of an image to be detected by the second detection region. Accordingly, the resolution of the first images acquired in the first detection region can be different from the resolution of the second images acquired in the second detection region, and thus the phase or scattering contrast image and the absorption image can each be generated with appropriate resolution.

In the aforementioned X-ray imaging apparatus according to this aspect, the detector preferably includes a scintillator configured to detect the X-rays and emits fluorescence, and a photodetector configured to detect the fluorescence, and the scintillator preferably has a different structure between a portion corresponding to the first detection region and a portion corresponding to the second detection region. Accordingly, the first detection region and the second detection region can have scintillator structures suitable for acquiring the first images and the second images, respectively, and thus the phase or scattering contrast image and the absorption image can each be generated in an appropriate state.

Effect of the Invention

According to the present invention, as described above, it is possible to significantly reduce or prevent a decrease in the accuracy of the diagnosis (evaluation) based on the images captured by the normal X-ray imaging and the X-ray phase imaging.

BRIEF DESCRIPTION OF THE DRAWINGS

FIG. 3(A) is a diagram showing a state in which a first detection region and a second detection region move relative to a subject to be imaged, FIG. 3(B) is a diagram showing a state in which the positions of the first detection region and the second detection region with respect to the subject are different from the positions in FIG. 3(A), and FIG. 3(C) is a diagram showing a state in which the positions of the first detection region and the second detection region with respect to the subject are different from the positions in FIGS. 3(A) and 3(B).

FIG. 4(A) is a diagram showing generation of an absorption image based on a plurality of second images, and FIG.

4(B) is a diagram showing generation of a phase contrast image based on a plurality of first images.

FIG. 5 is schematic view showing the overall configuration of an X-ray imaging apparatus according to a first modified example of the first embodiment.

FIG. 6(A) is a diagram showing a state in which a first detection region and a second detection region move relative to a subject to be imaged in the X-ray imaging apparatus according to the first modified example of the first embodiment, FIG. 6(B) is a diagram showing a state in which the positions of the first detection region and the second detection region with respect to the subject are different from the positions in FIG. 6(A), and FIG. 6(C) is a diagram showing a state in which the positions of the first detection region and the second detection region with respect to the subject are different from the positions in FIGS. 6(A) and 6(B).

FIG. 7 is a schematic view showing the overall configuration of an X-ray imaging apparatus according to a second modified example of the first embodiment.

FIG. 8(A) is a diagram showing a state in which a first detection region and a second detection region move relative to a subject to be imaged in an X-ray imaging apparatus according to the second modified example of the first embodiment, FIG. 8(B) is a diagram showing a state in which the positions of the first detection region and the second detection region with respect to the subject are different from the positions in FIG. 8(A), and FIG. 8(C) is a diagram showing a state in which the positions of the first detection region and the second detection region with respect to the subject are different from the positions in FIGS. 8(A) and 8(B).

Figure 9:
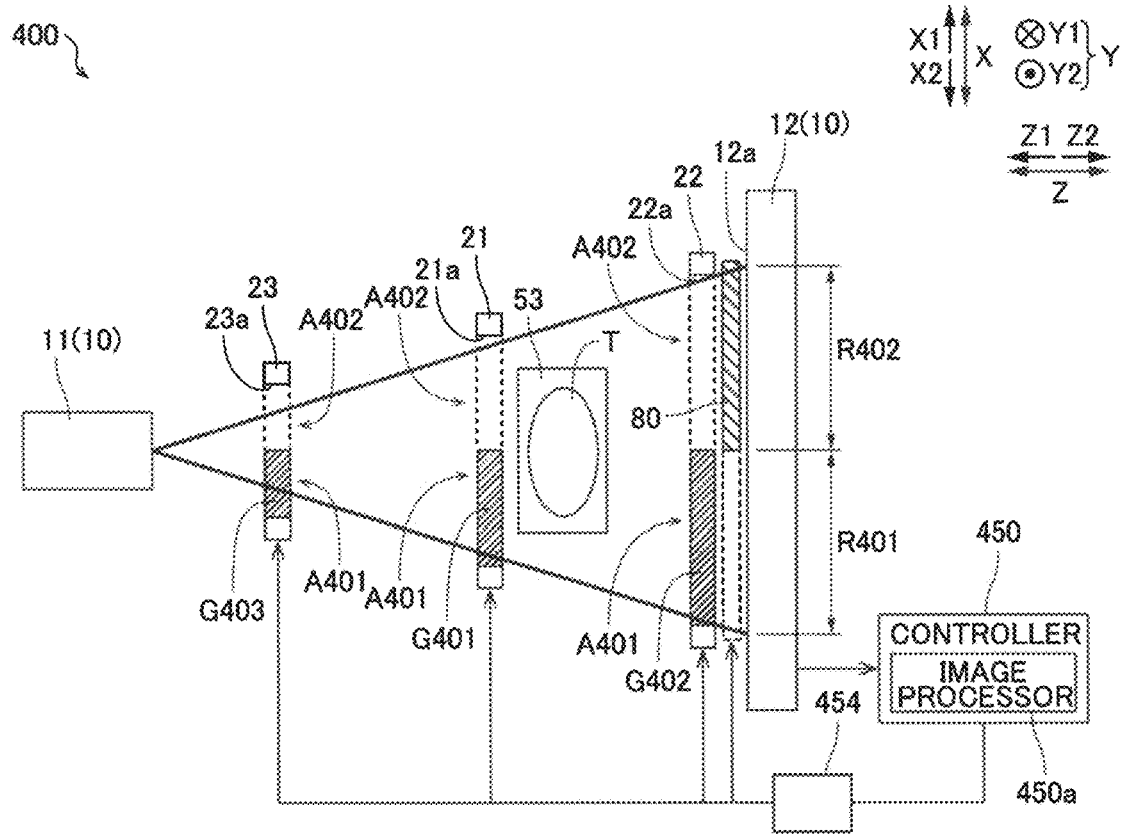

FIG. 9 is a schematic view showing the overall configuration of an X-ray imaging apparatus according to a second embodiment.

Figure 10:
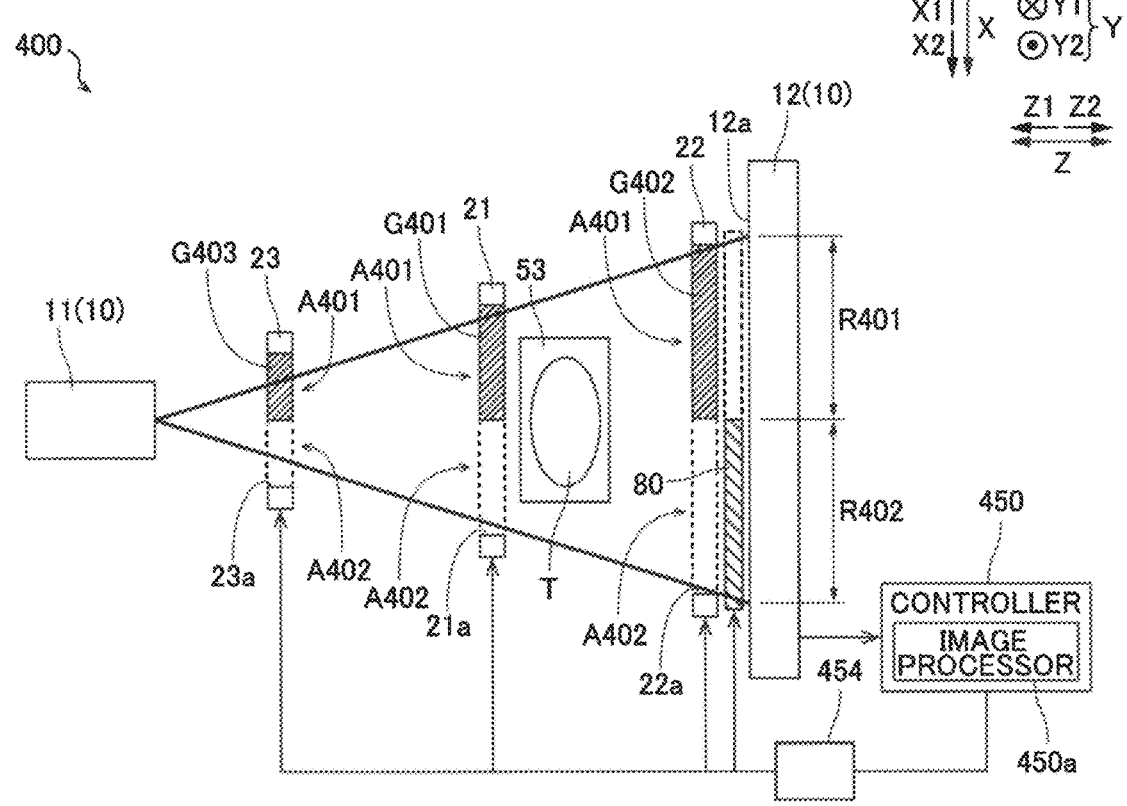

FIG. 10 is a diagram showing a state in which the positions of gratings are moved in the X-ray imaging apparatus according to the second embodiment.

Figure 11:
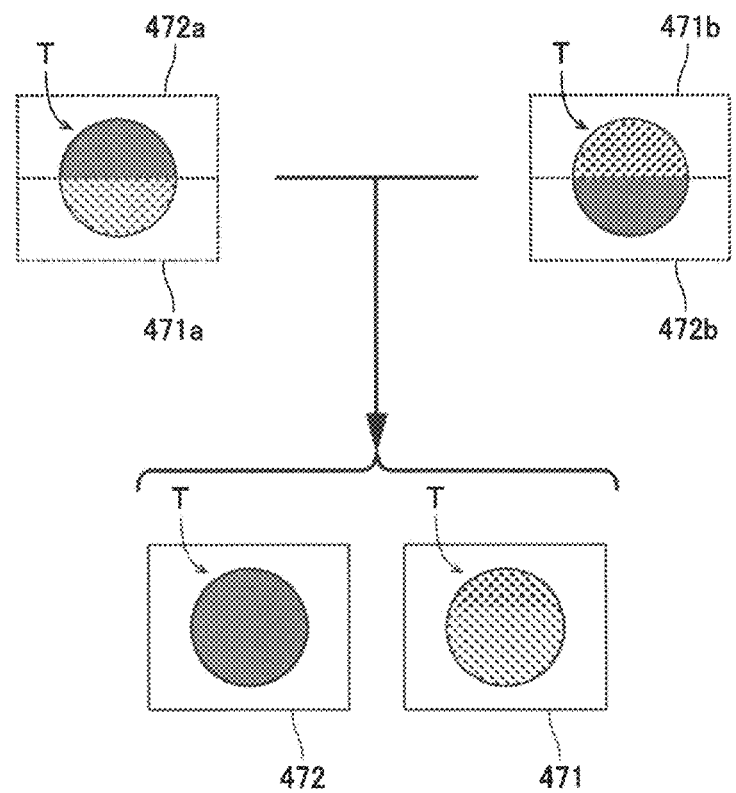

FIG. 11 is a diagram showing generation of a phase contrast image and an absorption image based on a plurality of first images and a plurality of second images in the X-ray imaging apparatus according to the second embodiment.

Figure 12:
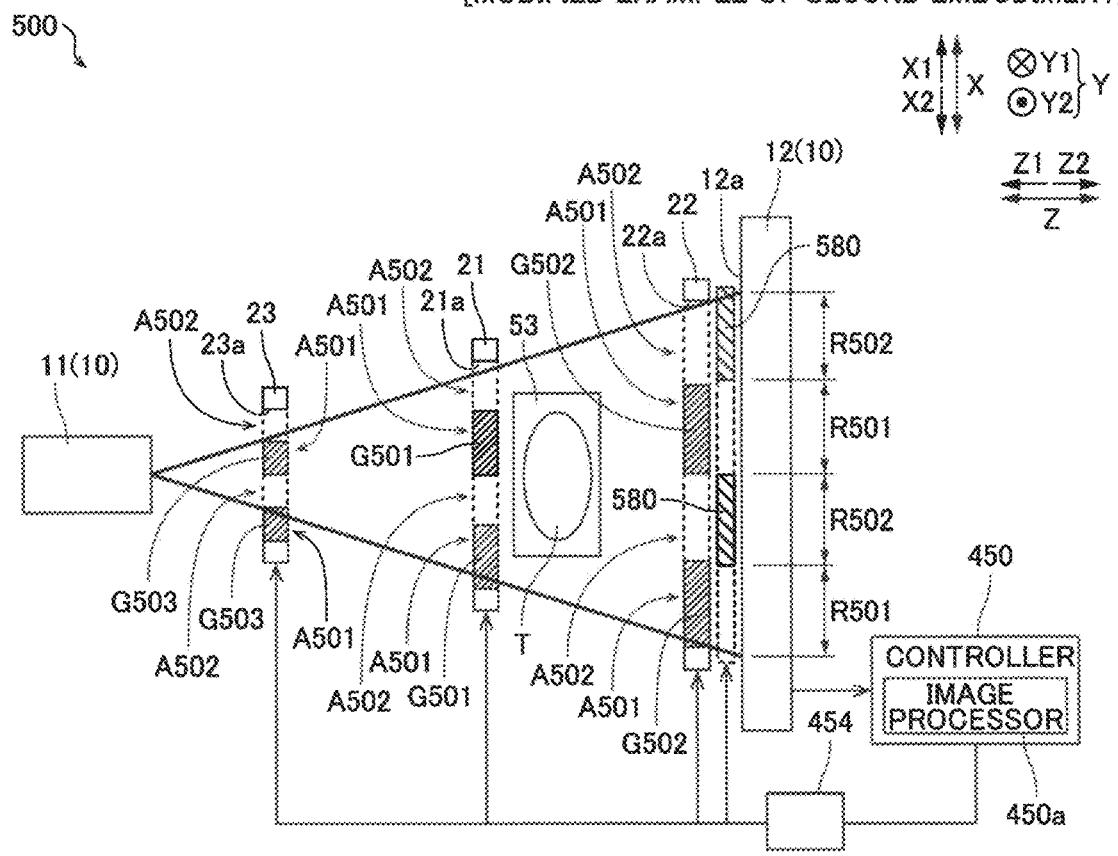

FIG. 12 is a schematic view showing the overall configuration of an X-ray imaging apparatus according to a modified example of the second embodiment.

Figure 13:
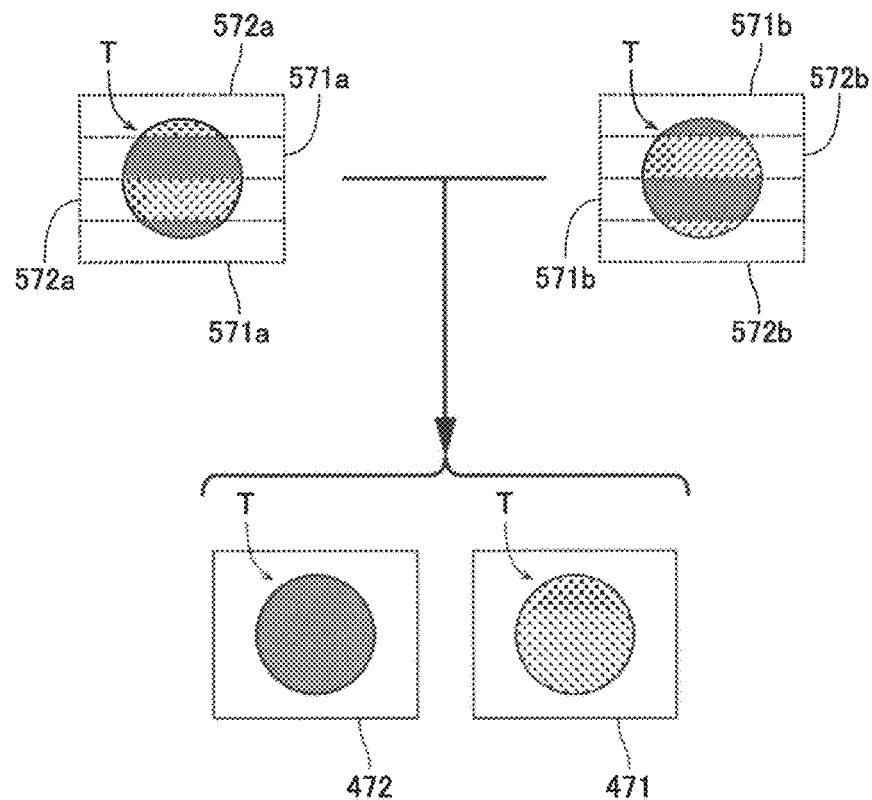

FIG. 13 is a diagram showing generation of a phase contrast image and an absorption image based on a plurality of first images and a plurality of second images in the X-ray imaging apparatus according to the modified example of the second embodiment.

Figure 14:
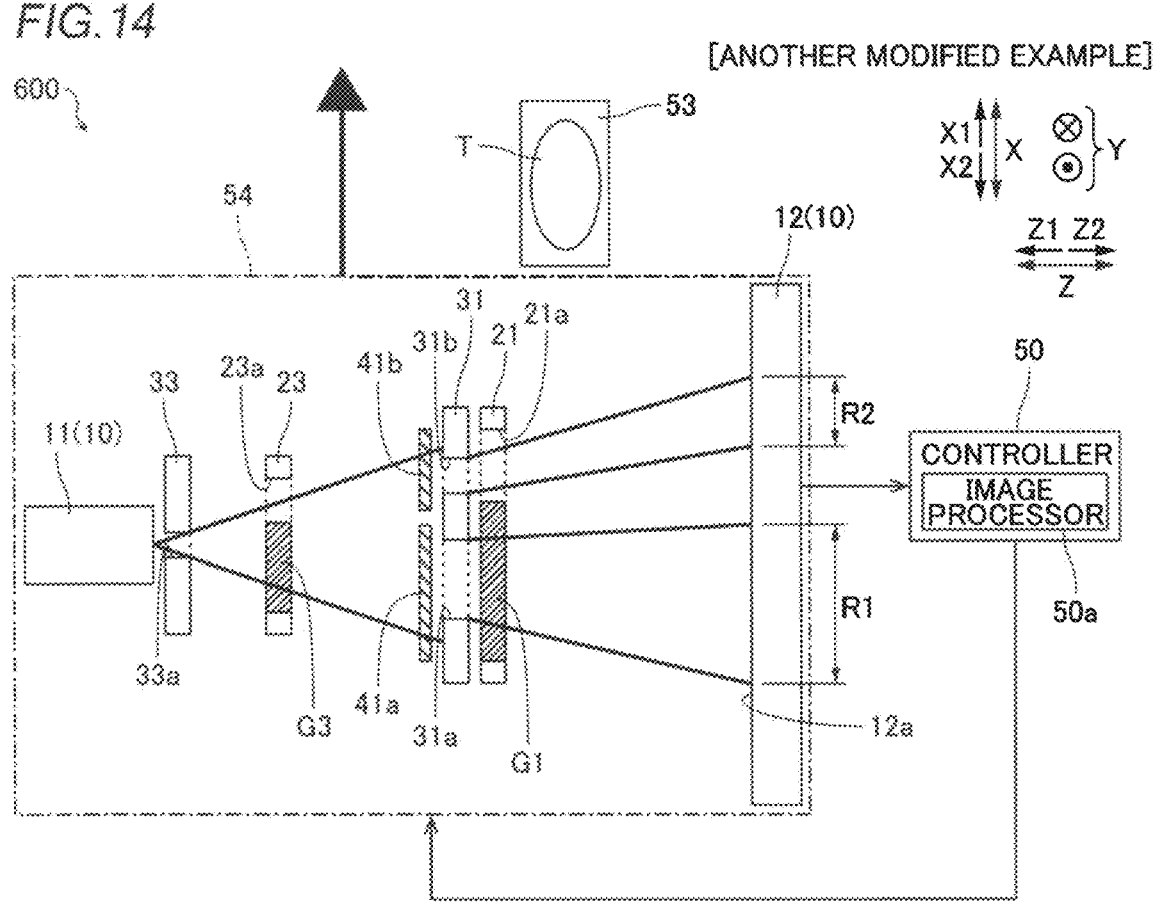

FIG. 14 is a diagram showing an X-ray imaging apparatus including no second grating according to a modified example of the first embodiment.

FIG. 15 is a diagram showing an X-ray imaging apparatus including no third grating according to another modified example of the first embodiment.

FIG. 16(A) is a diagram showing an X-ray imaging apparatus in which the orientations of a grating and an imager and the moving directions of the imager and the grating with respect to a subject to be imaged are different according to yet another modified example of the first embodiment.

FIG. 16(B) is a diagram showing an X-ray imaging apparatus in which the orientations of a grating and an imager and the moving directions of the imager and the grating with respect to a subject to be imaged are different according to yet another modified example of the first embodiment.

FIG. 16(C) is a diagram showing an X-ray imaging apparatus in which the orientations of a grating and an imager and the moving directions of the imager and the grating with respect to a subject to be imaged are different according to yet another modified example of the first embodiment.

Figure 17:
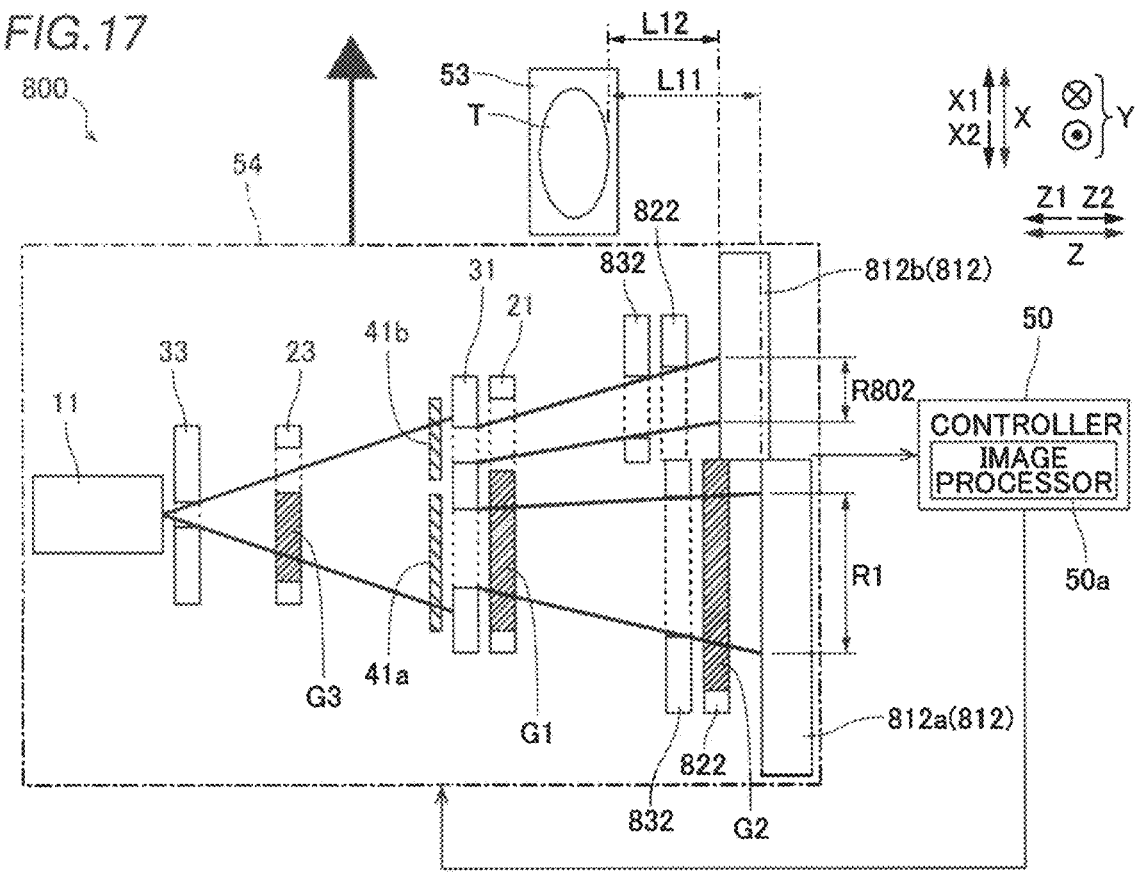

FIG. 17 is a diagram showing an X-ray imaging apparatus according to further another modified example of the first embodiment in which the distance of a second detection region from a subject to be imaged is smaller than the distance of a first detection region from the subject.

Figure 18:
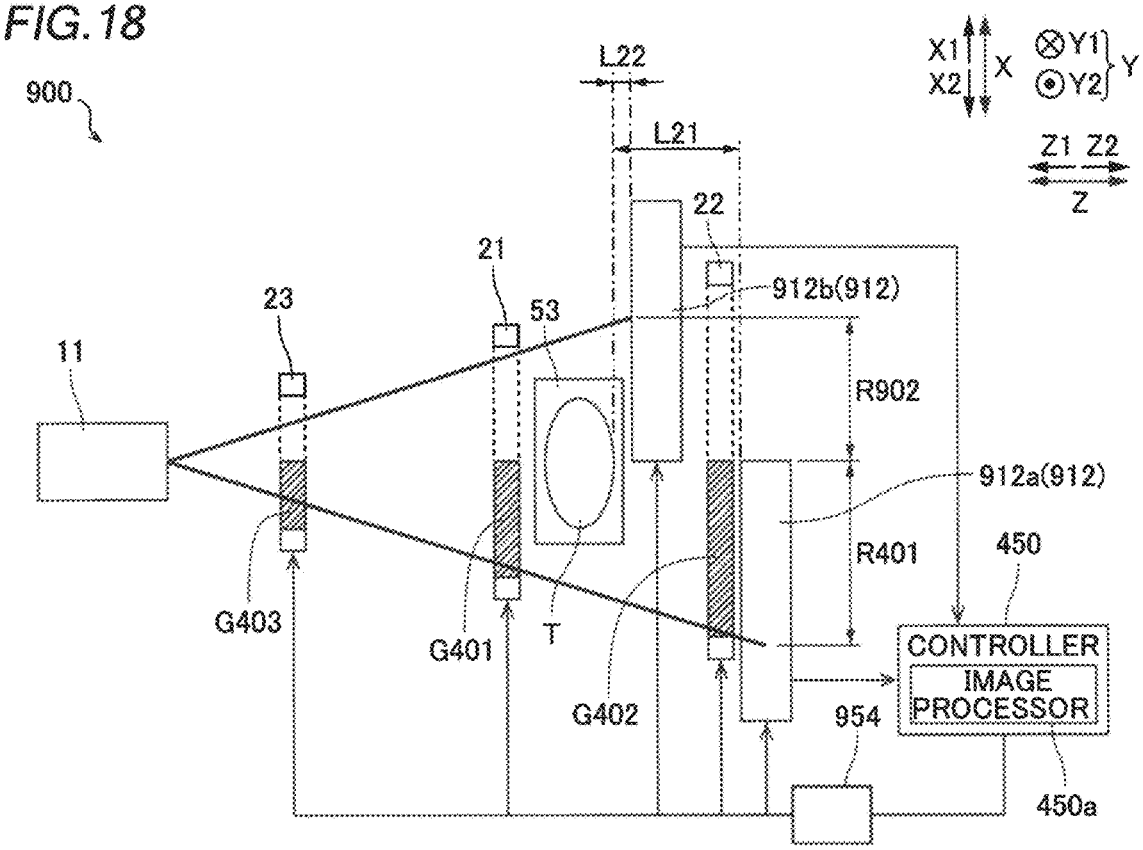

FIG. 18 is a diagram showing an X-ray imaging apparatus according to another modified example of the second embodiment in which the distance of a second detection region from a subject to be imaged is smaller than the distance of a first detection region from the subject.

Figure 19:
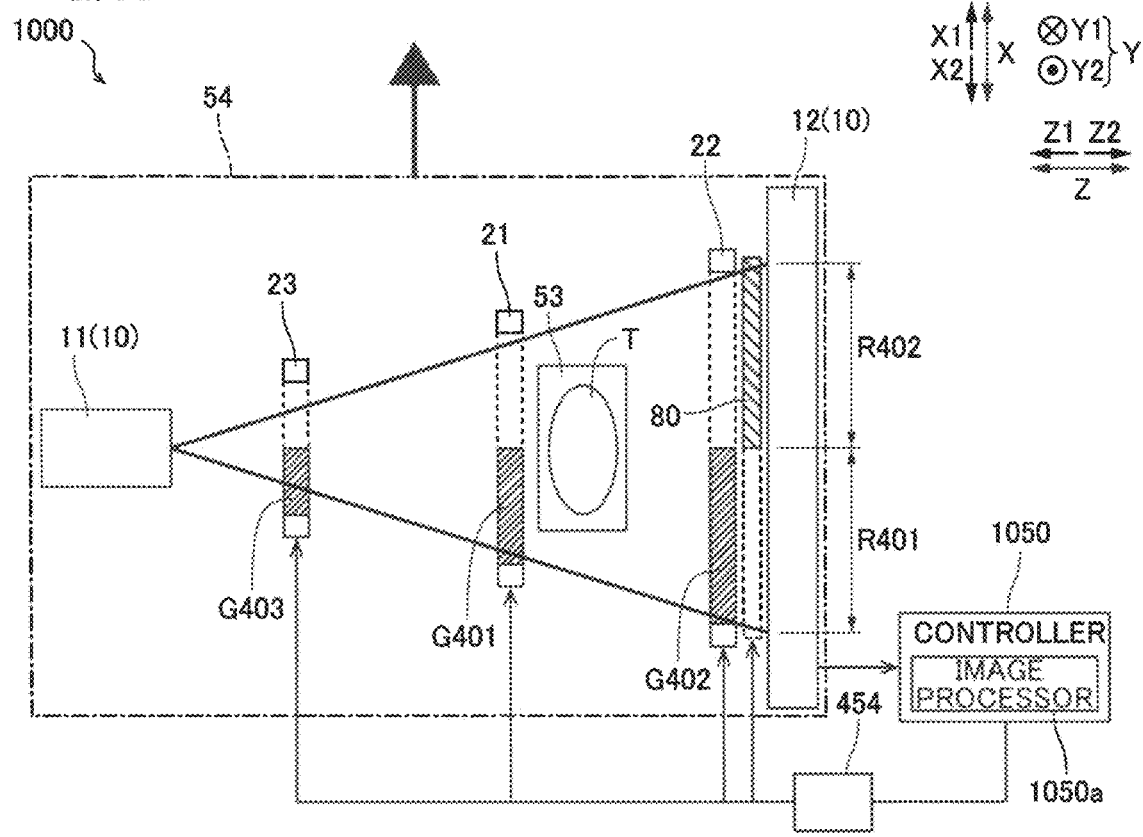

FIG. 19 is a diagram showing a state in which a first grating, a second grating, and a third grating are arranged on the X1 side in an X-ray imaging apparatus according to still another modified example of the second embodiment in which imaging is performed a plurality of times in each of a state in which the first grating, the second grating, and the third grating are arranged on the X1 side and a state in which the first grating, the second grating, and the third grating are arranged on the X2 side.

Figure 20:
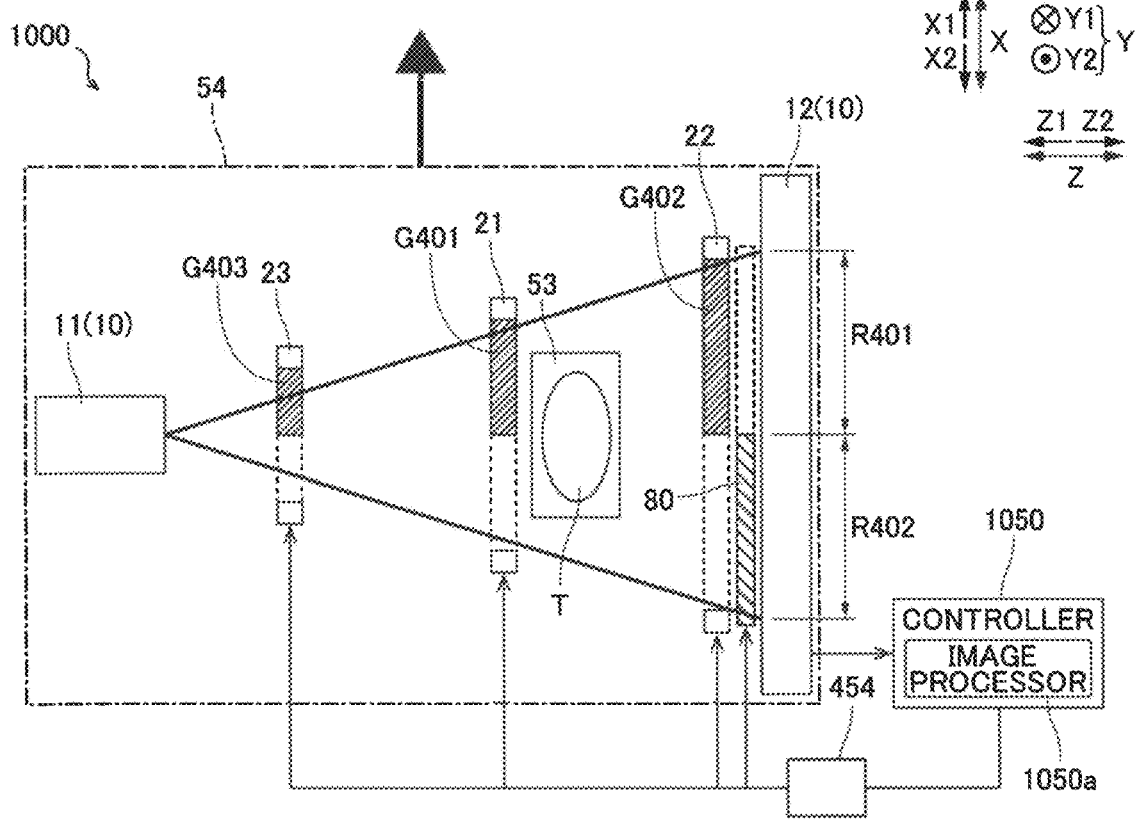

FIG. 20 is a diagram showing a state in which the first grating, the second grating, and the third grating are arranged on the X2 side in the X-ray imaging apparatus according to the modified example of the second embodiment in which imaging is performed a plurality of times in each of a state in which the first grating, the second grating, and the third grating are arranged on the X1 side and a state in which the first grating, the second grating, and the third grating are arranged on the X2 side.

MODES FOR CARRYING OUT THE INVENTION

Embodiments embodying the present invention are hereinafter described on the basis of the drawings.

First Embodiment

The configuration of an X-ray imaging apparatus 100 according to a first embodiment of the present invention is now described with reference to FIGS. 1 and 2. The X-ray imaging apparatus 100 is an imaging apparatus that can be used for breast cancer diagnosis in mammography. The X-ray imaging apparatus 100 is also an imaging apparatus that can be used for diagnosis in a medical examination other than breast cancer diagnosis, evaluation in non-destructive inspection, etc.

(Configuration of X-ray Imaging Apparatus)

Figure 1:
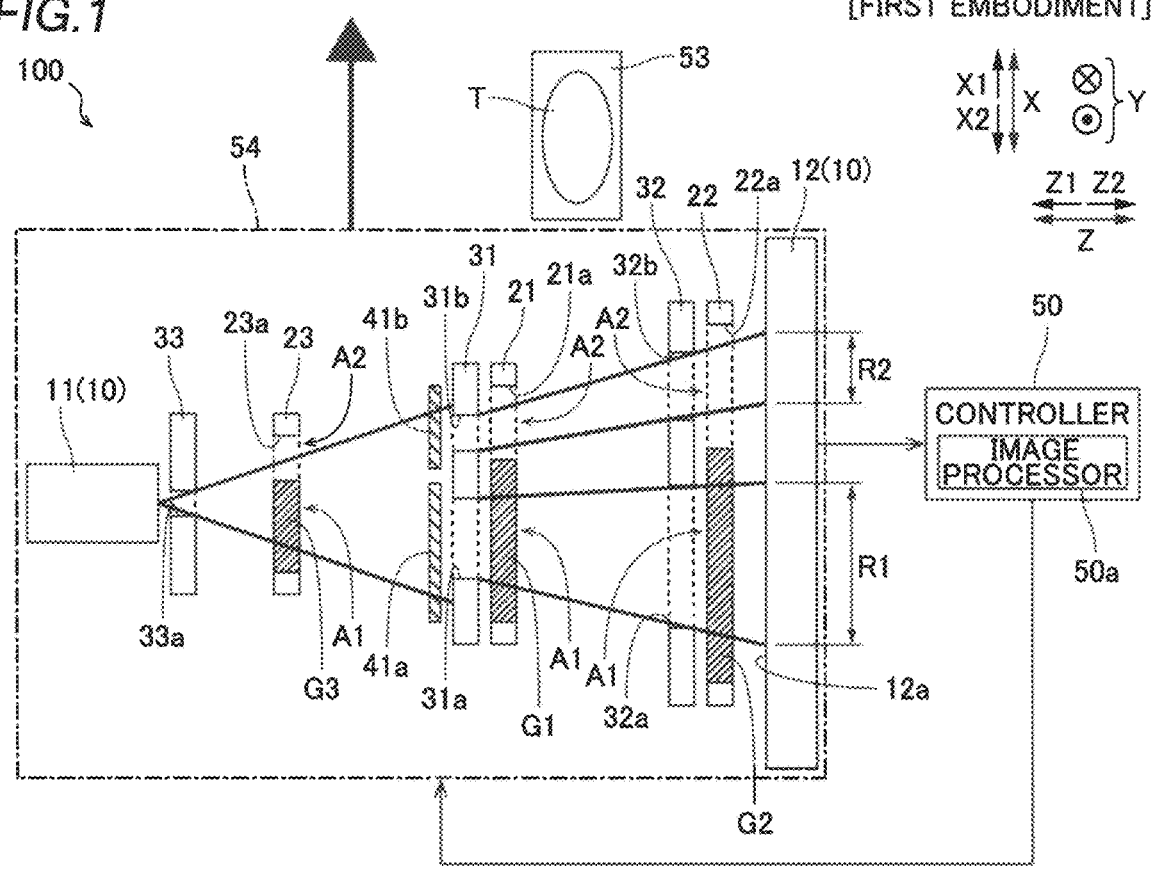
FIG. 1 is a schematic view showing the overall configuration of an X-ray imaging apparatus according to a first embodiment of the present invention.

As shown in FIG. 1, the X-ray imaging apparatus 100 includes an imager 10 including an X-ray source 11 and a detector 12, a plurality of grating holders including grating holders 21, 22, and 23, a plurality of collimators including collimators 31, 32, and 33, filters 41a and 41b, a controller 50, a subject stage 53, and a moving mechanism 54. The collimator 31 is an example of an "irradiation range adjustment member" in the claims. The filters 41a and 41b are examples of a "first filter" and a "second filter" in the claims, respectively. The moving mechanism 54 is an example of a "relative position changer" in the claims.

In the X-ray imaging apparatus 100, the X-ray source 11, the collimator 33, the grating holder 23, the filters 41a and 41b, the collimator 31, the grating holder 21, the collimator 32, the grating holder 22, and the detector 12 are aligned in this order in an X-ray irradiation axis direction (optical axis direction, Z direction). In this specification, a horizontal direction and a vertical direction orthogonal to the X-ray optical axis direction are defined as an X direction and a Y direction, respectively.

The X-ray source 11 generates X-rays when a high voltage is applied thereto. The X-rays generated by the X-ray source 11 are radiated in a direction (Z2 direction) in which the detector 12 is arranged.

The detector 12 detects the X-rays radiated from the X-ray source 11 and converts the detected X-rays into electrical signals. The detector 12 is a flat panel detector (FPD), for example. The detector 12 includes a plurality of conversion elements 12b (see FIG. 2(B)) arranged on a detection surface 12a on the X-ray source 11 side (Z1 side) and pixel electrodes (not shown) arranged on the plurality of conversion elements 12b. The plurality of conversion elements 12b and the pixel electrodes are aligned in the X direction and the Y direction at predetermined cycles (pixel pitches). Detection signals (image signals) are transmitted from the detector 12 to an image processor 50a included in the controller 50.

Figures 2A, 2B, 2C:
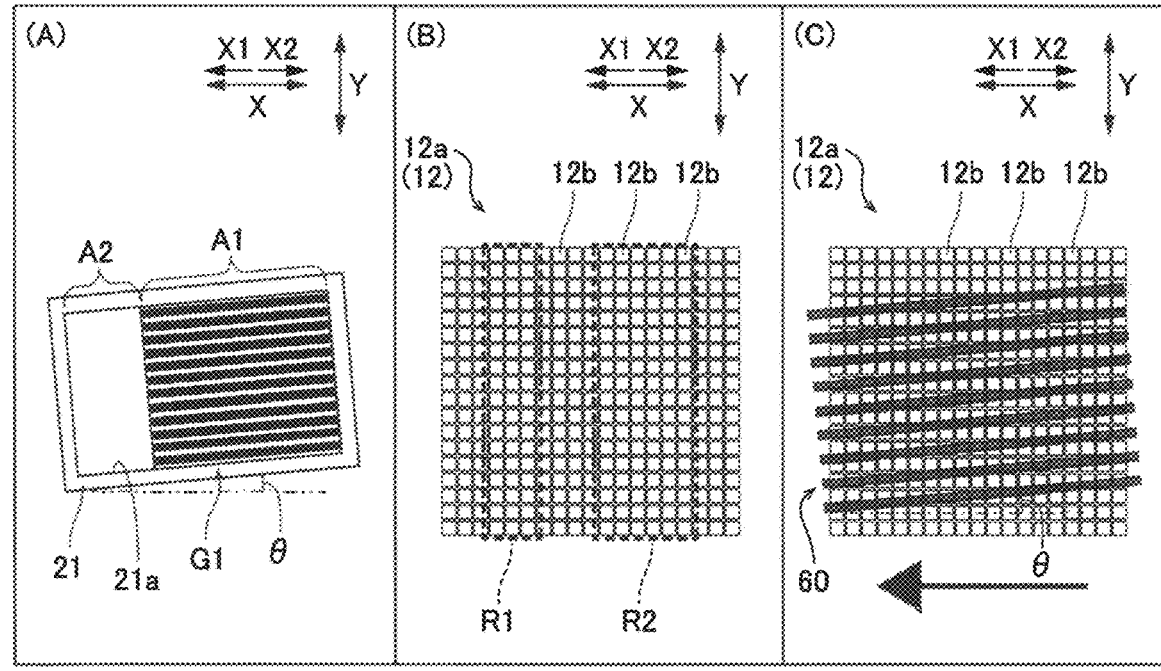
FIG. 2(A) is a diagram showing a grating holder that holds a first grating.
FIG. 2(B) is a diagram showing a detection surface of a detector.
FIG. 2(C) is a diagram showing the detection surface of the detector and a self-image by the first grating.

The grating holders 21, 22, and 23 include grating holding holes 21a, 22a, and 23a, respectively. The grating holding holes 21a, 22a, and 23a hold a first grating G1, a second grating G2, and a third grating G3, respectively. As shown in FIGS. 1 and 2(A), the first grating G1, the second grating G2, and the third grating G3 are smaller than the grating holding holes 21a, 22a, and 23a, respectively, substantially in the X direction. Thus, in each of the grating holding holes 21a, 22a, and 23a, a region A1 on the X2 side in which the grating is arranged and a region A2 on the X1 side in which no grating is arranged are formed.

The first grating G1 has a grating pattern so as to diffract the X-rays radiated from the X-ray source 11. Specifically, the first grating G1 is configured as a diffraction grating (phase grating) that changes the phases of X-rays that pass therethrough. As shown in FIG. 2(A), the first grating G1 includes slits and X-ray absorbers arranged in predetermined cycles (grating pitches) substantially in the Y direction. Each slit and each X-ray absorber extend substantially in the X direction.

The first grating G1 is arranged between the X-ray source 11 and the second grating G2, and is provided to form a self-image by the X-rays radiated from the X-ray source 11 (by the Talbot effect). Note that the Talbot effect indicates that when coherent X-rays pass through a grating in which slits are formed, a grating image (self-image) is formed at a position away from the grating by a predetermined distance (Talbot distance).

The second grating G2 includes a plurality of slits and X-ray absorbers arranged at predetermined cycles (grating pitches) substantially in the Y direction, similarly to the first grating G1. Each slit and each X-ray absorber extend substantially in the X direction.

The second grating G2 is arranged between the first grating G1 and the detector 12, and is provided to interfere with the self-image formed by the first grating G1. The second grating G2 is arranged at a position away from the first grating G1 by a Talbot distance in order to cause the self-image and the second grating G2 to interfere with each other. Note that the self-image formed by the first grating G1 and the second grating G2 interfere with each other such that moire 60 (see FIG. 2(C)) having cycles larger than the grating pitches of the self-image is formed on the detection surface 12a.

The third grating G3 is arranged between the X-ray source 11 and the first grating G1, and is configured as a grating (multi-slit) capable of micro-focusing the X-rays radiated from the X-ray source 11.

The collimator 31 includes a shielding member that shields X-rays. The collimator 31 includes collimator holes 31a and 31b configured to be freely opened and closed. The collimator hole 31a can adjust the irradiation range of the X-rays radiated from the X-ray source 11 to the detector 12 through the first grating G1. The collimator hole 31b can adjust the irradiation range of the X-rays radiated to the detector 12 without passing through the first grating G1. The collimator holes 31a and 31b are examples of a "first irradiation range adjuster" and a "second irradiation range adjuster" in the claims, respectively.

In the first embodiment, a first detection region R1 and a second detection region R2 of the detector 12 are configured to detect the X-rays that have passed through the first grating G1 and have reached the detector 12 and the X-rays that have reached the detector 12 without passing through the first grating G1, respectively. That is, in the detector 12, the first detection region R1 detects the X-rays that have passed through the region A1 on the X2 side in which the grating is arranged. The second detection region R2 detects the X-rays that have passed through the region A2 on the X1-side in which no grating is arranged. Thus, it is possible to detect X-rays for generating a phase contrast image 71 (see FIG. 4) and an absorption image 72 (see FIG. 4) in the first detection region R1 and the second detection region R2, respectively. In the first embodiment, as shown in FIG. 1, the first detection region R1 and the second detection region R2 are aligned in the X direction and are arranged apart from each other in the X direction. The phase contrast image 71 is an example of a "phase or scattering contrast image" in the claims.

The phase contrast image 71 is a general term for an image captured using the first grating G1 and/or the second grating G2, and includes an absorption image, a phase differential image, and a dark-field image. The absorption image is an X-ray image formed based on a difference in the degree of X-ray absorption by a subject T to be imaged. The phase differential image is an X-ray image formed based on an X-ray phase shift. The dark-field image is a visibility image obtained by a change in visibility based on small-angle scattering of an object. The dark-field image is also called a small-angle scattering image. The "visibility" denotes sharpness. Furthermore, the absorption image 72 generated based on the X-rays detected in the second detection region R2 is an image based on the X-rays that have reached the detector 12 without passing through a plurality of gratings including the first grating G1 as compared with the absorption image included in the phase contrast image 71, and thus the contrast is increased.

The collimator 32 includes collimator holes 32a and 32b configured to be freely opened and closed. The collimator holes 32a and 32b are formed so as to correspond to the region A1 in the grating holding hole 22a in which the grating is arranged and the region A2 in the grating holding hole 22a in which no grating is arranged, respectively, in the X direction. The collimator holes 32a and 32b have sizes substantially corresponding to the X-ray irradiation ranges adjusted by the collimator holes 31a and 31b. Thus, the collimator 32 can significantly reduce or prevent scattered rays other than the X-rays radiated from the X-ray source 11 from reaching the first detection region R1 and the second detection region R2 of the detector 12.

The collimator 33 includes a collimator hole 33a. The collimator hole 33a is provided to adjust the irradiation range of the X-rays generated from the X-ray source 11. Thus, it is possible to significantly reduce or prevent radiation of the X-rays generated from the X-ray source 11 in directions other than a direction toward the detection surface 12a of the detector 12.

In the first embodiment, the irradiation range of the X-rays reaching the second detection region R2 adjusted by the collimator hole 31b is smaller than the irradiation range of the X-rays reaching the first detection region R1 adjusted by the collimator hole 31a. Specifically, the size of the collimator hole 31b is smaller than the size of the collimator hole 31a. In other words, in the X direction, the second detection region R2 is smaller than the first detection region R1. Accordingly, the X-ray irradiation range narrowed by the collimator hole 31b is smaller than the X-ray irradiation range narrowed by the collimator hole 31a, and thus the irradiation range of the X-rays reaching the second detection region R2 is smaller than the irradiation range of the X-rays reaching the first detection region R1.

The filter 41a is arranged in the vicinity of the X-ray source 11 side (Z1 side) of the collimator hole 31a, and is configured to change the spectrum of the X-rays that pass through the collimator hole 31a. The filter 41b is arranged in the vicinity of the X-ray source 11 side (Z1 side) of the collimator hole 31b, and is configured to change the spectrum of the X-rays that pass through the collimator hole 31b. Thus, it is possible to adjust the spectrum of the X-rays reaching the first detection region R1 and the second detection region R2. In the X-ray imaging apparatus 100, the filter 41a and the filter 41b adjust the incident X-rays such that the spectrum of the incident X-rays is suitable for generating the phase contrast image 71 and the absorption image 72, respectively. In the first embodiment, the filter 41a and the filter 41b are each arranged at a predetermined position with respect to the first grating G1 in the Z-axis direction.

The controller 50 includes the image processor 50a capable of generating an X-ray image. The controller 50 is configured to control the operation of the moving mechanism 54. The controller 50 includes a central processing unit (CPU), a read only memory (ROM), a random access memory (RAM), etc., for example.

The image processor 50a is configured to generate the phase contrast image 71 and the absorption image 72 as X-ray images based on the detection signals transmitted from the detector 12. The image processor 50a includes a processor such as a graphics processing unit (GPU) or a field-programmable gate array (FPGA) configured for image processing, for example.

The subject stage 53 has a placement surface that can hold the subject T. The subject stage 53 may include a holding mechanism for the subject stage 53 such as a chuck mechanism or a hand mechanism (not shown). For example, when the X-ray imaging apparatus 100 is configured as a mammography apparatus, the subject stage 53 includes a breast holder configured to hold the breast.

The moving mechanism 54 is configured to be able to move structures (each portion included in a one-dot chain line in FIG. 1) from the X-ray source 11 to the detector 12 aligned in the optical axis direction (Z direction) substantially in the X direction, as shown by a thick arrow in FIG. 1. That is, in the first embodiment, the moving mechanism 54 can move the imager 10 including the X-ray source 11 and the detector 12 and the first grating G1 with respect to the subject T placed on the subject stage 53 so as to change the relative positions of the first detection region R1 and the second detection region R2 with respect to the subject T. Specifically, the moving mechanism 54 is configured to continuously change the relative positions of the imager 10 and the first grating G1 with respect to the subject T in a predetermined direction (X direction) by continuously moving the imager 10 and the first grating G1 in the predetermined direction (X direction) in a state in which the relative position of the first grating G1 with respect to the imager 1 is maintained.

In the X-ray imaging apparatus 100, a direction in which the grating of the first grating G1 extends is inclined with respect to a direction in which the conversion elements 12b of the detector 12 are aligned, and the imager 10 including the first grating G1 and the detector 12 moves in the direction in which the conversion elements 12b of the detector 12 are aligned with respect to the subject T. Specifically, the direction in which the grating of the first grating G1 extends is inclined at an angle θ with respect to the X direction, as shown in FIG. 2(A). A direction in which the grating of the second grating G2 extends is also inclined at the angle θ with respect to the X direction. Furthermore, as shown in FIG. 2(B), the detector 12 is arranged in such a manner that the direction in which the conversion elements 12b are aligned is in the X direction and the Y direction. Thus, the self-image diffracted by the first grating G1 and the moire 60 generated by the second grating G2 are inclined at the angle θ with respect to the X direction, as shown in FIG. 2(C). In this state, the imager 10 including the first grating G1 and the detector 12 is moved in an X1 direction (the direction of a thick arrow in FIG. 2(C)) with respect to the subject T by the moving mechanism 54. Consequently, the moving mechanism 54 can move the imager unit 10 including the X-ray source 11 and the detector 12 and the first grating G1 with respect to the subject T.

(Generation of Phase Contrast Image and Absorption Image)

Generation of the phase contrast image 71 and the absorption image 72 in the X-ray imaging apparatus 100 is now described in detail with reference to FIGS. 2 to 4.

As described above, the moving mechanism 54 is configured to change the relative positions of the first detection region R1 and the second detection region R2 with respect to the subject T by moving, in the X direction, the structures from the X-ray source 11 to the detector 12 aligned in the optical axis direction (Z direction). That is, as shown in FIG. 3, the positions of the first detection region R1 and the second detection region R2 can be moved in the X direction with respect to the subject T.

The first detection region R1 and the second detection region R2 of the detector 12 are configured to function as line sensors of multi-line pixels. That is, as shown in FIG. 2, the first detection region R1 and the second detection region R2 are regions formed in a rectangular shape having short sides in the X direction and long sides in the Y direction on the detection surface 12a. The X-ray imaging apparatus 100 detects the X-rays reaching the first detection region R1 and the second detection region R2 while moving the first detection region R1 and the second detection region R2 in the X direction with respect to the subject T. Thus, the image processor 50a can obtain a plurality of first images 71a and a plurality of second images 72a, as shown in FIG. 4. In addition, the image processor 50a can generate the phase contrast image 71 obtained by reconstructing the plurality of first images 71a and the absorption image 72 obtained by reconstructing the plurality of second images 72a based on the plurality of first images 71a and the plurality of second images 72a, respectively. Consequently, the phase contrast image 71 and the absorption image 72 corresponding to a moving range in the X direction by the moving mechanism 54 are generated. In the X-ray imaging apparatus 100, as shown in FIG. 3, the moving mechanism 54 moves in such a manner that the first detection region R1 and the second detection region R2 pass through the subject T such as shown in FIG. 4, the phase contrast image 71 and the absorption image 72 including the entire subject T can be generated.

In the X-ray imaging apparatus 100, the controller 50 is configured to perform normal X-ray imaging halfway and to be able to select whether or not to perform X-ray phase imaging based on an image generated by the normal X-ray imaging. Specifically, in the first embodiment, the moving mechanism 54 is configured to change the relative positions of the first detection region R1 and the second detection region R2 with respect to the subject T in such a manner that the detector 12 detects X-rays from the side of the second detection region R2 among the first detection region R1 and the second detection region R2.

More specifically, the first detection region R1 and the second detection region R2 are aligned on the X2 side and the X1 side, respectively, along a direction (X direction) in which the relative positions of the imager 10 and the first grating G1 with respect to the subject T are continuously changed, as described above. Thus, in the second detection region R2, detection of X-rays is started before the first detection region R1, and thus acquisition of the second images 72a can be started before acquisition of the first images 71a. As described above, the collimator holes formed in the plurality of collimators including the collimator 31 are configured to be freely opened and closed. Therefore, the controller 50 can determine whether or not to radiate X-rays to the first detection region R1 by confirming the previously acquired second images 72a (absorption image 72) and opening or closing the collimator hole 31a according to the need of the first images 71a (phase contrast image 71). In the first embodiment, the first detection region R1 and the second detection region R2 are arranged apart from each other in the X direction, and thus the controller 50 can easily ensure the processing time from confirming the first images 71a to determining whether or not to radiate X-rays to the first detection region R1.

Advantages of First Embodiment

In the first embodiment, the following advantages are obtained.

In the first embodiment, as described above, the image processor 50a is configured to generate the phase contrast image 71 based on the plurality of first images 71a acquired by the first detection region R1 at a plurality of relative positions with respect to the subject T, and to generate the absorption image 72 based on the plurality of second images 72a acquired by the second detection region R2 at the plurality of relative positions with respect to the subject T. Accordingly, the phase contrast image 71 and the absorption image 72 can be generated based on the first images 71a and the second images 72a acquired at the same time, and thus the imaging position of the subject T for each image in the normal X-ray imaging and the imaging position of the subject T for each image in the X-ray phase imaging can be easily matched. Consequently, as compared with the case in which the normal X-ray imaging and the X-ray phase imaging are performed by separate apparatuses, it is possible to easily match the imaging positions of the subject T for each image, and thus a decrease in the accuracy of the diagnosis (evaluation) based on the images captured by the normal X-ray imaging and the X-ray phase imaging can be significantly reduced or prevented. Accordingly, in diagnosis in a medical examination, evaluation in nondestructive examinations, etc., when the same subject T has a portion that is likely to be depicted in only one of the absorption image and the phase differential and dark-field images and a portion that is likely to be depicted in only the other of the absorption image and the phase differential and dark-field images, the diagnosis (evaluation) can be performed with high accuracy. In addition, the absorption image and the phase differential image or the dark-field image are combined, or contrast enhancement and spatial frequency processing using information from other images (such as information about a portion or structure that appears to be a cancer) are performed such that the diagnostic ability can be improved.

In the first embodiment, as described above, the image processor 50a is configured to generate the dark-field image (phase contrast image 71) based on the plurality of first images 71a acquired by the first detection region R1 at the plurality of relative positions with respect to the subject T, and to generate the absorption image 72 based on the plurality of second images 72a acquired by the second detection region R2 at the plurality of relative positions with respect to the subject T. Accordingly, the absorption image generated by the normal X-ray imaging and the dark-field image generated by the X-ray phase imaging can be easily generated in a state in which the imaging positions of the subject are matched. Consequently, it is possible to significantly reduce or prevent a decrease in the accuracy of the diagnosis (evaluation) based on the absorption image 72 generated by the normal X-ray imaging and the dark-field image generated by the X-ray phase imaging. Thus, for example, in the diagnosis of breast cancer, the absorption image 72 for determining whether a tumor is benign or malignant and the dark-field image that is excellent in depiction of calcification and cancer boundaries are combined such that the diagnosis is performed with high accuracy.

In the first embodiment, as described above, the moving mechanism 54 is configured to change the relative positions of the first detection region R1 and the second detection region R2 with respect to the subject T by moving the imager 10 including the X-ray source 11 and the detector 12 and the first grating G1 with respect to the subject T. Accordingly, the relative positions of the first detection region R1 and the second detection region R2 with respect to the subject T can be easily changed by the moving mechanism 54.

In the first embodiment, as described above, the moving mechanism 54 is configured to continuously change the relative positions of the imager 10 and the first grating G1 with respect to the subject T in the predetermined direction (X1 direction) by continuously moving the imager 10 and the first grating G1 in the predetermined direction (X1 direction) in a state in which the relative position of the first grating G1 with respect to the imager 10 is maintained. Furthermore, the image processor 50a is configured to generate the phase contrast image 71 and the absorption image 72 based on the plurality of first images 71a and the plurality of second images 72a, respectively, generated by continuous changes of the relative positions of the imager 10 and the first grating G1 with respect to the subject T by the moving mechanism 54. Accordingly, the plurality of first images 71a and the plurality of second images 72a aligned in the predetermined direction (X direction) can be acquired by continuously changing the relative positions of the imager 10 and the first grating G1 with respect to the subject T in the predetermined direction (X1 direction). Consequently, a large-area phase contrast image 71 and a large-area absorption image 72 can be easily generated based on the plurality of first images 71a and the plurality of second images 72a aligned in the predetermined direction (X direction), respectively. Furthermore, the phase contrast image 71 can be generated simply by continuously changing the relative positions of the imager 10 and the first grating G1 with respect to the subject T in the predetermined direction (X1 direction), and thus the X-ray phase imaging can be performed without precise adjustment of the positional relationship between the imager 10 and the first grating G1 for forming the self-image by the first grating G1.

In the first embodiment, as described above, the first detection region R1 and the second detection region R2 are aligned along the direction (X direction) in which the relative positions of the imager 10 and the first grating G1 with respect to the subject T are continuously changed. Furthermore, the moving mechanism 54 is configured to change the relative positions in such a manner that the detector 12 detects X-rays from the side of the second detection region R2 among the first detection region R1 and the second detection region R2. Accordingly, acquisition of the second images 72a in the second detection region R2 can be started before acquisition of the first images 71a in the first detection region R1, and thus it is possible to determine, based on the absorption image 72 based on the second images 72a captured halfway, whether or not it is necessary to generate the phase contrast image 71 based on the first images 71a acquired after the second images 72a. Consequently, when it is determined from a part of the absorption image 72 that the phase contrast image 71 is unnecessary, only the normal X-ray imaging for generating the absorption image 72 is performed continuously, and the X-ray phase imaging for generating the phase contrast image 71 is not performed such that unnecessary X-ray radiation to the subject T can be significantly reduced or prevented. Thus, in diagnosis in a medical examination, for example, it is possible to significantly reduce or prevent an increase in the X-ray dose to which a patient is exposed.

In the first embodiment, as described above, the X-ray imaging apparatus 100 includes the collimator 31 arranged on the X-ray source 11 side (Z1 side) with respect to the subject T between the X-ray source 11 and the first grating G1 and including the collimator hole 31a configured to adjust the irradiation range of the X-rays reaching the first detection region R1 and the collimator hole 31b configured to adjust the irradiation range of the X-rays reaching the second detection region R2. Accordingly, the collimator hole 31a and the collimator hole 31b can easily adjust the irradiation range of the X-rays reaching the first detection region R1 and the second detection region R2, respectively. Consequently, the total amounts of X-rays that respectively reach the first detection region R1 and the second detection region R2 can be easily adjusted so as to be optimum amounts for generating the phase contrast image 71 and the absorption image 72.

In the first embodiment, as described above, the collimator hole 31a and the collimator hole 31b are arranged apart from each other along the direction (X direction) in which the relative positions of the imager 10 and the first grating G1 with respect to the subject T are continuously changed. Accordingly, the collimator hole 31a and the collimator hole 31b are arranged apart from each other, and thus as compared with the case in which the collimator hole 31a and the collimator hole 31b are not arranged apart from each other, adjustment of the X-ray irradiation range by the collimator hole 31a and adjustment of the X-ray irradiation range by the collimator hole 31b can be easily and independently performed. Furthermore, the collimator hole 31a and the collimator hole 31b are arranged apart from each other along the direction (X direction) in which the relative positions of the imager 10 and the first grating G1 with respect to the subject T are continuously changed, and thus the time for determining, based on the absorption image 72 based on the second images 72a captured halfway, whether or not it is necessary to generate the phase contrast image 71 based on the first images 71a acquired after the second images 72a can be easily ensured.

In the first embodiment, as described above, the irradiation range of the X-rays reaching the second detection region R2 adjusted by the collimator hole 31b is smaller than the irradiation range of the X-rays reaching the first detection region R1 adjusted by the collimator hole 31a. Accordingly, the amount of X-rays reaching the second detection region R2 can be smaller than the amount of X-rays reaching the first detection region R1, and thus when both the phase contrast image 71 based on the first images 71a and the absorption image 72 based on the second images 72a are generated, it is possible to significantly reduce or prevent radiation, to the subject T, of X-rays other than those necessary for image generation.

In the first embodiment, as described above, the X-ray imaging apparatus 100 includes the filter 41a arranged on the X-ray source 11 side (Z1 side) with respect to the subject T and configured to adjust the spectrum of the X-rays radiated to the first detection region R1, and the filter 41b arranged on the X-ray source 11 side (Z1 side) with respect to the subject T and configured to adjust the spectrum of the X-rays reaching the second detection region R2. Accordingly, regardless of the spectrum of the X-rays radiated from the X-ray source 11, the spectrum of the X-rays reaching the first detection region R1 and the second detection region R2 can be easily adjusted individually to the spectrum of X-rays suitable for generating the phase contrast image 71 based on the first images 71a and the absorption image 72 based on the second images 72a.

In the first embodiment, as described above, the X-ray imaging apparatus 100 includes the second grating G2 arranged between the first grating G1 and the detector 12 and configured to interfere with the self-image of the first grating G1. Accordingly, the self-image of the first grating G1 and the second grating G2 interfere with each other, and thus the moire 60 having a pitch larger than that of the self-image of the first grating G1 can be formed. Consequently, the formed moire 60 is detected such that as compared with the case in which the self-image of the first grating G1 is directly detected, an increase in the detection accuracy of the detector 12 required for the phase contrast image 71 can be significantly reduced or prevented.

First Modified Example of First Embodiment

A first modified example of the first embodiment is now described with reference to FIGS. 5 and 6. In the first modified example of the first embodiment, an example including a collimator 231 in which one collimator hole 31a and a plurality of collimator holes 231b are formed is described unlike the X-ray imaging apparatus 100 according to the first embodiment including the collimator 31 in which one collimator hole 31a and one collimator hole 31b are formed. In the figures, the same configurations as those of the first embodiment are denoted by the same reference numerals.

An X-ray imaging apparatus 200 according to the first modified example of the first embodiment includes collimators 231 and 232 instead of the collimators 31 and 32 of the X-ray imaging apparatus 100. The collimator 231 includes one collimator hole 31a and the plurality of (two) collimator holes 231b. The collimator 232 includes one collimator hole 32a and a plurality of (two) collimator holes 232b. The collimator 231 is an example of an "irradiation range adjustment member" in the claims. The collimator hole 231b is an example of a "second irradiation range adjuster" in the claims.

In the X-ray imaging apparatus 200, X-ray imaging and X-ray phase imaging are performed with the plurality of collimator holes 231b and 232b opened (a state in FIG. 5) such that as shown in FIG. 6, a phase contrast image 71 and absorption images 72 can be generated based on X-rays detected by a first detection region R1 and a plurality of (two) second detection regions R2. That is, in the first modified example of the first embodiment, two absorption images 72 shown in FIG. 4 can be acquired concurrently by the two second detection regions R2. These absorption images 72 are added such that it is possible to ensure twice the exposure time with the same imaging time.

In the first modified example of the first embodiment, the plurality of collimator holes 231b are configured to adjust the irradiation ranges of X-rays reaching the second detection regions R2 by changing the number of collimator holes 231b that transmit X-rays. Specifically, the collimator 231 is configured to be able to change a state in which both of the two collimator holes 231b are opened and a state in which one of the two collimator holes 231b is opened and the other of the collimator holes 231b is closed. The collimator holes 232b formed in the collimator 232 are configured to open and close so as to correspond to the opened and closed states of the collimator holes 231b. Thus, it is possible to easily adjust the irradiation ranges of the X-rays reaching the second detection regions R2.

The remaining configurations of the first modified example of the first embodiment are similar to those of the aforementioned first embodiment.

Advantages of First Modified Example of First Embodiment

In the first modified example of the first embodiment, the following advantages are obtained.

In the first modified example of the first embodiment, as described above, the X-ray imaging apparatus 200 includes one collimator hole 31a and the plurality of collimator holes 231b, and the plurality of collimator holes 231b are configured to adjust the irradiation ranges of the X-rays reaching the second detection regions R2 by changing the number of collimator holes 231b that transmit the X-rays. Accordingly, the collimator holes 231b can easily adjust the amount of X-rays reaching the second detection regions R2 without passing through the grating in order to generate the absorption images 72. Consequently, when there is a difference in the amount of X-rays necessary for generating the absorption images 72 due to a difference in a subject T to be imaged, the amount of X-rays used to generate the absorption images 72 after reaching the second detection regions R2 can be easily adjusted to an optimum amount of X-rays for each subject T to be imaged.

The remaining advantages of the first modified example of the first embodiment are similar to those of the aforementioned first embodiment.

Second Modified Example of First Embodiment

A second modified example of the first embodiment is now described with reference to FIGS. 7 and 8. In the second modified example of the first embodiment, an example is described in which in a plurality of gratings, the positions of regions in which the gratings are arranged and the positions of regions in which no grating is arranged are different from those in the X-ray imaging apparatus 200 according to the first modified example of the first embodiment. In the figures, the same configurations as those of the first embodiment and the first modified example of the first embodiment are denoted by the same reference numerals.

An X-ray imaging apparatus 300 according to the second modified example of the first embodiment includes grating holders 321, 322, and 323 instead of the grating holders 21, 22, and 23 of the X-ray imaging apparatus 200 according to the first modified example of the first embodiment. The grating holders 321, 322, and 323 include grating holding holes 21a, 22a, and 23a, respectively, similarly to the grating holders 21, 22, and 23 of the X-ray imaging apparatus 200. In each of the grating holding holes 21a, 22a, and 23a, a region A302 in which no grating (a first grating G301, a second grating G302, and a third grating G303) is arranged, a region A301 in which the grating is arranged, and a region A 302 in which no grating is arranged are aligned in this order along an X direction.

The X-ray imaging apparatus 300 according to the second modified example of the first embodiment includes a collimator 331 and a collimator 332. The collimator 331 includes a collimator hole 231a and a plurality of collimator holes 231b so as to correspond to the region A301 in which the grating is arranged and the region A302 in which no grating is arranged in the grating holding hole 21a formed in the grating holder 321. The collimator 332 includes a collimator hole 232a and a plurality of collimator holes 232b so as to correspond to the region A301 in which the grating is arranged and the region A302 in which no grating is arranged in the grating holding hole 22a formed in the grating holder 22.

In the X-ray imaging apparatus 300, X-ray imaging and X-ray phase imaging are performed with the plurality of collimator holes 231b and 232b opened (a state in FIG. 7) such that as shown in FIG. 8, a phase contrast image 71 and absorption images 72 can be generated based on X-rays detected by a first detection region R1 and a plurality of (two) second detection regions R2.

In the X-ray imaging apparatus 300, the second detection regions R2 are arranged on both sides (X1 side and X2 side) of the first detection region R1 so as to sandwich the first detection region R1, and thus even when a moving mechanism 54 is moved with respect to a subject T to be imaged in either a direction toward the X1 side or a direction toward the X2 side, acquisition of second images 72a can be started before acquisition of first images 71a.

The remaining configurations of the second modified example of the first embodiment are similar to those of the aforementioned first embodiment and the aforementioned first modified example of the first embodiment.

Advantages of Second Modified Example of First Embodiment

In the second modified example of the first embodiment, the following advantages are obtained.

In the second modified example of the first embodiment, as described above, the second detection regions R2 are arranged on both sides (the X1 side and the X2 side) so as to sandwich the first detection region R1 along a direction (X direction) in which the relative positions of an imager 10 and the first grating G301 with respect to the subject T are continuously changed. Accordingly, even when the position of the subject T and the positions of the imager 10 and the first grating G1 are reversed, normal X-ray imaging can be started before the X-ray phase imaging while the relative positions of the imager 10 and the first grating G1 with respect to the subject T are changed.

The remaining advantages of the second modified example of the first embodiment are similar to those of the aforementioned first embodiment and the aforementioned first modified example of the first embodiment.

Second Embodiment

A second embodiment is now described with reference to FIGS. 9 to 11. In the second embodiment, an example is described in which a first grating G401 is moved with respect to a subject T to be imaged and an imager 10 unlike the first embodiment in which the imager 10 including the X-ray source 11 and the detector 12 and the first grating G1 are moved with respect to the subject T in order to change the relative positions of the first detection region R1 and the second detection region R2 with respect to the subject T. In the figures, the same configurations as those of the first embodiment are denoted by the same reference numerals.

As shown in FIG. 9, an X-ray imaging apparatus 400 according to the second embodiment includes the imager 10 including an X-ray source 11 and a detector 12, a plurality of grating holders including grating holders 21, 22, and 23, a scattered-ray grid 80, a controller 450, and a moving mechanism 454. The scattered-ray grid 80 is an example of an "anti-scatter member" in the claims. The moving mechanism 454 is an example of a "relative position changer" in the claims.

The grating holders 21, 22, and 23 include grating holding holes 21a, 22a, and 23a, respectively, similarly to the first embodiment. The grating holding holes 21a, 22a, and 23a hold the first grating G401, a second grating G402, and a third grating G403, respectively. As shown in FIG. 9, the first grating G401, the second grating G402, and the third grating G403 are respectively smaller than the grating holding holes 21a, 22a, and 23a substantially in an X direction, and are respectively about half the sizes of the holes. Thus, in each of the grating holding holes 21a, 22a, and 23a, a region A401 on the X2 side in which the grating is arranged and a region A402 on the X1 side in which no grating is arranged are formed in substantially the same size.

In the second embodiment, as shown in FIG. 9, a first detection region R401 and a second detection region R402 of the detector 12 are configured to detect X-rays that have passed through the first grating G401 and have reached the detector 12 and X-rays that have reached the detector 12 without passing through the first grating G401 (with passing through the region S402 in which no grating is arranged), respectively. That is, in the first detection region R401 and the second detection region R402, X-rays for generating a phase contrast image 471 (see FIG. 11) and an absorption image 472 (see FIG. 11) can be respectively detected. The phase contrast image 471 is an example of a "phase or scattering contrast image" in the claims.

The scattered-ray grid 80 is configured to remove scattered rays other than X-rays radiated from the X-ray source 11. The scattered-ray grid 80 is arranged at a position corresponding to the second detection region R402 in the X direction among the first detection region R401 and the second detection region R402.

The controller 450 includes an image processor 450a capable of generating an X-ray image. The controller 450 is configured to control the operation of the moving mechanism 454. The image processor 450a is configured to generate the phase contrast image 471 and the absorption image 472 as X-ray images based on detection signals transmitted from the detector 12.

The moving mechanism 454 is configured to be able to move the first grating G401, the second grating G402, and the third grating G403 in the X direction in the grating holders 21, 22, and 23, respectively. That is, in the second embodiment, the moving mechanism 454 is configured to change the relative positions of the first detection region R401 and the second detection region R402 with respect to the subject T by moving the first grating G401 with respect to the subject T and the imager 10.

Specifically, the first grating G401, the second grating G402, and the third grating G403 are configured to be slidable to the X1 side and the X2 side in the grating holding holes 21a, 22a, and 23a. Accordingly, the first grating G401, the second grating G402, and the third grating G403 can be arranged on the X1 side (a state in FIG. 9) and on the X2 side (a state in FIG. 10).

(Generation of Phase Contrast Image and Absorption Image)

Generation of the phase contrast image 471 and the absorption image 472 in the X-ray imaging apparatus 400 is now described in detail with reference to FIG. 11.

In the second embodiment, the imager 10 is configured to perform imaging a plurality of times (twice). A first image 471a (471b) and a second image 472a (472b) are generated in a state in which the relative positions of the first detection region R401 and the second detection region R402 with respect to the subject T are changed by the moving mechanism 454 such that the relative positions are different in each imaging.

Specifically, the image processor 450a acquires the first image 471a and the second image 472a shown in the upper left of FIG. 11 by the X-rays detected in the first detection region R401 and the second detection region R402, respectively, in a state in which the first grating G401, the second grating G402, and the third grating G403 are arranged on the X1 side (the state in FIG. 9). In addition, the image processor 450a acquires the first image 471b and the second image 472b shown in the upper right of FIG. 11 by the X-rays detected in the first detection region R401 and the second detection region R402, respectively, in a state in which the first grating G401, the second grating G402, and the third grating G403 are arranged on the X2 side (the state in FIG. 10). Note that the imaging positions for the first image 471b and the second image 472b are opposite to the imaging positions for the first image 471a and the second image 472a shown in the upper left of FIG. 11, respectively.

As shown in a lower portion of FIG. 11, the image processor 450a generates the phase contrast image 471 by combining the first image 471a acquired in a state in which the first grating G401, the second grating G402, and the third grating G403 are arranged on the X1 side (the state in FIG. 9) with the first image 471b acquired in a state in which the first grating G401, the second grating G402, and the third grating G403 are arranged on the X2 side (the state in FIG. 10). In addition, the image processor 450a generates the absorption image 472 by combining the second image 472a acquired in a state in which the first grating G401, the second grating G402, and the third grating G403 are arranged on the X1 side (the state in FIG. 9) with the second image 472b acquired in a state in which the first grating G401, the second grating G402, and the third grating G403 are arranged on the X2 side (the state in FIG. 10). Consequently, the phase contrast image 471 and the absorption image 472 are generated with sizes larger than the region A401 in which the grating is arranged and the region A402 in which no grating is arranged.

The remaining configurations of the second embodiment are similar to those of the aforementioned first embodiment.

Advantages of Second Embodiment

In the second embodiment, the following advantages are obtained.

In the second embodiment, as described above, the image processor 450a is configured to generate the phase contrast image 471 based on the plurality of first images 471a acquired by the first detection region R401 at the plurality of relative positions with respect to the subject T, and to generate the absorption image 472 based on the plurality of second images 472a acquired by the second detection region R402 at the plurality of relative positions with respect to the subject T. Accordingly, the phase contrast image 471 and the absorption image 472 can be generated based on the first image 471a (471b) and the second image 472a (472b) acquired at the same time, and thus the imaging position of the subject T for each image in the normal X-ray imaging and the imaging position of the subject T for each image in the X-ray phase imaging can be easily matched. Consequently, similarly to the first embodiment, as compared with the case in which the normal X-ray imaging and the X-ray phase imaging are performed by separate apparatuses, the imaging positions of the subject T for each image can be easily matched, and thus it is possible to significantly reduce or prevent a decrease in the accuracy of the diagnosis (evaluation) based on the images captured by the normal X-ray imaging and the X-ray phase imaging.

In the second embodiment, as described above, the moving mechanism 454 is configured to change the relative positions of the first detection region R401 and the second detection region R402 with respect to the subject T by moving the first grating G401 with respect to the subject T and the imager 10. Accordingly, similarly to the first embodiment, the relative positions of the first detection region R401 and the second detection region R402 with respect to the subject T can be easily changed by the moving mechanism 454.

In the second embodiment, as described above, the imager 10 is configured to perform imaging a plurality of times, and generate the first image 471a (471b) and the second image 472a (472b) in a state in which the relative positions of the first detection region R401 and the second detection region R402 with respect to the subject T are changed by the moving mechanism 454 such that the relative positions are different in each imaging. Accordingly, the plurality of first images 471a (471b) and the plurality of second images 472a (472b) acquired by performing imaging a plurality of times and for which the relative positions are different can be acquired. Consequently, a large-area phase contrast image 471 and a large-area absorption image 472 can be easily generated based on the plurality of first images 471a (471b) and the plurality of second images 472a (472b) for which the relative positions are different, respectively. In addition, the region of the detector 12 necessary for generating the phase contrast image 471 or the absorption image 472 can be matched with the sum of the first detection region R401 and the second detection region R402, and thus a distance in which the first grating G1 is moved can be decreased as compared with the case in which the first grating G1 is completely retracted from the X-ray irradiation range in order to perform the normal X-ray imaging separately from the X-ray phase imaging. Consequently, it is possible to reliably significantly reduce or prevent an increase in the total imaging time for performing the normal X-ray imaging and the X-ray phase imaging.

In the second embodiment, as described above, the X-ray imaging apparatus 400 includes the scattered-ray grid 80 arranged at the position corresponding to the second detection region R402 among the first detection region R401 and the second detection region R402 and configured to remove the scattered rays. Accordingly, it is possible to significantly reduce or prevent the scattered rays other than the X-rays radiated from the X-ray source 11 and reaching the second detection region R402 without passing through the first grating G401 from reaching the second detection region R402. Consequently, it is possible to significantly reduce or prevent generation of noise in the absorption image 472 due to the influence of the scattered rays.

The remaining advantages of the second embodiment are similar to those of the aforementioned first embodiment.

Modified Example of Second Embodiment

A modified example of the second embodiment is now described with reference to FIGS. 12 and 13. In the modified example of the second embodiment, an example is described in which two regions A501 in which the grating is arranged and two regions A502 in which no grating is arranged are aligned in an X direction in each grating holder unlike the X-ray imaging apparatus 400 according to the aforementioned second embodiment in which one region A401 in which the grating is arranged and one region A402 in which no grating is arranged are aligned in the X direction in each grating holder. In the figures, the same configurations as those of the second embodiment are denoted by the same reference numerals.

In an X-ray imaging apparatus 500 according to the modified example of the second embodiment, a plurality of (two) first gratings G501, a plurality of (two) second gratings G502, and a plurality of (two) third gratings G503 are provided in the X direction. The first gratings G501, the second gratings G502, and the third gratings G503 are alternately arranged in the X direction. Specifically, as shown in FIG. 12, the first gratings G501, the second gratings G502, and the third gratings G503 are provided in grating holding holes 21a, 22a, and 23a, respectively, and the region A501 in which the grating (the first grating G501, the second grating G502, or the third grating G503) is arranged, the region A502 in which no grating is arranged, the region A501 in which the grating is arranged, and the region A502 in which no grating is arranged are arranged in this order from the X2 side toward the X1 side. Accordingly, in a detector 12, first detection regions R501 and second detection regions R502 are arranged in order of the first detection region R501, the second detection region R502, the first detection region R501, and the second detection region R502 from the X2 side toward the X1 side. In the X-ray imaging apparatus 500, scattered-ray grids 580 are arranged at positions corresponding to the second detection regions R502 in the X direction among the first detection regions R501 and the second detection regions R502, similarly to the X-ray imaging apparatus 400.

In the X-ray imaging apparatus 500, an image processor 450a acquires first images 571a and second images 572a shown in the upper left of FIG. 13 by X-rays detected in the first detection regions R501 and the second detection regions R502, respectively, in a state in which the first gratings G501, the second gratings G502, and the third gratings G503 are arranged as shown in FIG. 12. In addition, the image processor 450a acquires first images 571b and second images 572b shown in the upper right of FIG. 13 by X-rays detected in the first detection regions R501 and the second detection regions R502, respectively, in a state in which the arrangement of the first gratings G501, the second gratings G502, and the third gratings G503 (the arrangement of the regions A501 in which the grating is arranged and the regions A502 in which no grating is arranged) is reversed from the arrangement shown in FIG. 12. Note that the imaging positions for the first images 571b and the second image 572b are opposite to the imaging positions for the first images 571a and the second images 572a shown in the upper left of FIG. 13.

As shown in a lower portion of FIG. 13, the image processor 450a generates a phase contrast image 471 by combining the first images 571a acquired in a state in which the first gratings G501, the second gratings G502, and the third gratings G503 are arranged as shown in FIG. 12 with the first images 571b acquired in a state in which the arrangement of the regions A501 in which the grating is arranged and the regions A502 in which no grating is arranged is reversed from the arrangement shown in FIG. 12. In addition, the image processor 450a generates an absorption image 472 by combining the second images 572a acquired in a state in which the first gratings G501, the second gratings G502, and the third gratings G503 are arranged as shown in FIG. 12 with the second images 572b acquired in a state in which the arrangement of the regions A501 in which the grating is arranged and the regions A502 in which no grating is arranged is reversed from the arrangement shown in FIG. 12.

The remaining configurations of the modified example of the second embodiment are similar to those of the aforementioned second embodiment.

Advantages of Modified Example of Second Embodiment

In the modified example of the second embodiment, the following advantages are obtained.

In the modified example of the second embodiment, as described above, the plurality of first detection regions R501 and the plurality of second detection regions R502 are alternately arranged. Accordingly, the first detection regions R501 and the second detection regions R502 are alternately arranged, and thus the positions of the first detection regions R501 and the positions of the second detection regions R502 at the second imaging are reversed from those at the first imaging such that it is possible to generate the phase contrast image 471 and the absorption image 472 respectively having sizes of imaging ranges obtained by combining the first images 571a (571b) acquired by the first detection regions R501 with the second images 572a (572b) acquired by the second detection regions R502 by performing imaging only twice. Furthermore, the plurality of first detection regions R501 and the plurality of second detection regions R502 are provided, and thus distances in which each first grating G501, each second grating G502, and each third grating G503 are moved at the first imaging and the second imaging can be decreased as compared with the case in which the plurality of first gratings G501, the plurality of second gratings G502, and the plurality of third gratings G503 are not provided. Consequently, it is possible to reliably significantly reduce or prevent an increase in the total imaging time for performing X-ray imaging and X-ray phase imaging.

The remaining advantages of the modified example of the second embodiment are similar to those of the aforementioned second embodiment.

Other Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the example in which the moving mechanism 54 changes the relative positions of the first detection region R1 and the second detection region R2 with respect to the subject T by moving the imager 10 including the X-ray source 11 and the detector 12 and the first grating G1 with respect to the subject T has been shown in the aforementioned first embodiment, the present invention is not limited to this. In the present invention, the relative positions of the first detection region and the second detection region with respect to the subject may be changed by moving the subject with respect to the imager and the first grating.

While the example in which the collimators 31 and 32 respectively include one collimator hole 31b and one collimator hole 32b configured to adjust the irradiation range of the X-rays reaching the second detection region R2 has been shown in the aforementioned first embodiment, and the example in which the collimators 231 and 232 include respectively the two collimator holes 231b and the two collimator holes 232b configured to adjust the irradiation ranges of the X-rays reaching the second detection regions R2 has been shown in each of the aforementioned first and second modified examples of the first embodiment, the present invention is not limited to this. In the present invention, the number of collimator holes configured to adjust the irradiation range(s) of the X-rays reaching the second detection region(s) may be three or more.

While the examples in which the second grating G2 and the second grating G402 (G502) are provided have been shown in the aforementioned first and second embodiments, the present invention is not limited to this. In the present invention, as in an X-ray imaging apparatus 600 shown in FIG. 14, no second grating may be provided. In this case, for example, as shown in FIG. 14, a collimator arranged in the vicinity of the X-ray source side of a second grating may be omitted. Note that the X-ray imaging apparatus 600 is a modified example of the first embodiment.

While the examples in which the third grating G3 and the second grating G403 (G503) are provided have been shown in the aforementioned first and second embodiments, the present invention is not limited to this. In the present invention, as in an X-ray imaging apparatus 700 shown in FIG. 15, no third grating may be provided. In this case, X-ray micro-focus cannot be achieved by a third grating, and thus a high-output X-ray source having a large focus size may not be used. Note that the X-ray imaging apparatus 700 is a modified example of the first embodiment.

While the example in which the collimator 33 is provided has been shown in the aforementioned first embodiment, and the example in which no collimator is arranged in the vicinity of the X-ray source 11 has been shown in the aforementioned second embodiment, the present invention is not limited to this. In the present invention, in the configuration of the first embodiment, no collimator may be arranged in the vicinity of the X-ray source. In the configuration of the second embodiment, a collimator may be arranged in the vicinity of the X-ray source.

While the example in which the direction in which the grating of the first grating G1 extends and the direction in which the conversion elements 12b of the detector 12 are aligned are inclined, and the imager 10 including the first grating G1 and the detector 12 moves in the direction in which the conversion elements 12b of the detector 12 are aligned with respect to the subject T has been shown in the aforementioned first embodiment, the present invention is not limited to this. In the present invention, for example, as shown in FIG. 16, a direction in which the grating of a first grating G1 extends may coincide with a direction in which conversion elements 12b of a detector are aligned, and an imager including the first grating G1 and the detector 12 may move in a direction inclined with respect to the direction in which the conversion elements 12b of the detector 12 are aligned with respect to a subject T to be imaged.

While the example in which imaging is performed twice has been shown in the aforementioned second embodiment, the present invention is not limited to this. In the present invention, imaging may be performed three or more times. In this case, the moving distance of the grating can be decreased, and an increase in the size of the grating can be significantly reduced or prevented.

While the example in which the two first gratings G501, the two second gratings G502, and the two third gratings G503 are arranged in the X direction has been shown in the modified example of the aforementioned second embodiment, the present invention is not limited to this. In the present invention, three first gratings, three second gratings, and three third gratings may be arranged in the X direction.

While the example in which the grating that diffracts X-rays is used has been shown in each of the aforementioned first and second embodiments, the present invention is not limited to this. In the present invention, a grating that shields X-rays may be used.

While a technique in which the second grating for interfering with the self-image generated by the phase grating is provided is used to detect the X-rays diffracted by the phase grating (first grating) in each of the aforementioned first and second embodiments, the present invention is not limited to this. In the present invention, a technique in which the self-image is directly detected using a detector having fine pixels may be used. In other words, in the present invention, the resolution of an image to be detected by the first detection region can be different from the resolution of an image to be detected by the second detection region. Accordingly, the resolution of the first images acquired in the first detection region can be different from the resolution of the second images acquired in the second detection region, and thus the phase or scattering contrast image and the absorption image can each be generated with appropriate resolution. For example, the region (second detection region) for acquiring the absorption image does not need to have fine pixels, and thus an increase in the number of pixels can be significantly reduced or prevented by using a general detector that does not have fine pixels.

While a technique in which the second grating for interfering with the self-image generated by the phase grating is provided is used to detect the X-rays diffracted by the phase grating (first grating) in each of the aforementioned first and second embodiments, the present invention is not limited to this. In the present invention, a technique in which a detector having a grid-like scintillator is used to interfere with the self-image may be used. In other words, in the present invention, the detector may include a scintillator configured to detect X-rays and emit fluorescence, and a photodetector configured to detect the fluorescence, and the scintillator may have a different structure between a portion corresponding to the first detection region and a portion corresponding to the second detection region. Accordingly, the first detection region and the second detection region can have scintillator structures suitable for acquiring the first images and the second images, respectively, and thus the phase or scattering contrast image and the absorption image can each be generated in an appropriate state. For example, the region (second detection region) for acquiring the absorption image does not need to have a grid-like scintillator, and thus the detection sensitivity can be improved by using a scintillator having a general structure that is not grid-like.

While the example in which the filter 41a and the filter 41b are respectively arranged at the predetermined positions with respect to the first grating G1 in the Z-axis direction has been shown in the aforementioned first embodiment, the present invention is not limited to this. In the present invention, the relative position between the first grating G1 and the filter 41a may be different from the relative position between the first grating G1 and the filter 41b. In this case, an adjustment mechanism configured to adjust the relative position between the first grating G1 and the filter 41a and the relative position between the first grating G1 and the filter 41b may be provided. Thus, the relative positions of the filter 41a and the filter 41b with respect to the first grating G1 can be adjusted such that the spectrum of the X-rays radiated from the X-ray source 11 is appropriately filtered.

While the example in which the first detection region R1 (R401) and the second detection region R2 (R402) are aligned in the X direction has been shown in each of the aforementioned first and second embodiments, the present invention is not limited to this. In the present invention, the first detection region and the second detection region may not be aligned in the X direction. In this case, for example, as in an X-ray imaging apparatus 800 (900) shown in FIG. 17 (FIG. 18), the distance L12 (L22) of a second detection region R802 (R902) from a subject T to be imaged may be smaller than the distance L11 (L21) of a first detection region R401 from the subject T. Note that the X-ray imaging apparatuses 800 and 900 are modified examples of the first and second embodiments, respectively.

As shown in FIG. 17, the X-ray imaging apparatus 800 includes a detector 812, a grating holder 822, and a collimator 832. The detector 812 includes a detector portion 812a and a detector portion 812b, the positions of which are different from each other in a Z direction such that the distances of the first detection region R1 and the second detection region R802 from the subject T in the ZZ direction are different from each other. The detector portion 912a is arranged in such a manner that a distance between a surface of the detector portion 912a on the first grating G1 side and the subject T is the distance L11. The detector portion 912b is arranged in such a manner that a distance between a surface of the detector portion 912b on the first grating G1 side and the subject T is the distance L12 (smaller than the distance L11). The grating holder 822 includes portions, the positions of which are different from each other in the Z direction so as to correspond to the detector portion 812a and the detector portion 812b. The collimator 832 includes portions, the positions of which are different from each other in the Z direction so as to correspond to the detector portion 812a and the detector portion 812b.

As shown in FIG. 18, the X-ray imaging apparatus 900 includes a detector 912 and a moving mechanism 954. The detector 912 includes a detector portion 912a and a detector portion 912b, the positions of which are different from each other in the Z direction such that the distances of the first detection region R401 and the second detection region R902 from the subject T in the Z direction are different from each other. The detector portion 912a is arranged in such a manner that a distance between a surface of the detector portion 912a on the first grating G1 side and the subject T is the distance L21. The detector portion 912b is arranged in such a manner that the distance between a surface of the detector portion 912b on the first grating G1 side and the subject T is the distance L22 (smaller than the distance L21). The moving mechanism 954 is configured to move the detector portion 912a and the detector portion 912b in an X direction so as to correspond to movement of a first grating G401, a second grating G402, and a third grating G403 in the X direction when changing the relative positions of the first detection region R401 and the second detection region R902 with respect to the subject T.

With the aforementioned configuration of the X-ray imaging apparatus 800 (900), the distance L12 (L22) of the second detection region R802 (R902) from the subject T can be relatively small, and thus it is possible to significantly reduce or prevent an increase in the subject T's penumbra (image blurring) caused by the focal point size of the X-ray source and generated in the absorption image detected in the second detection region R802 (R902).

While the example in which imaging is performed by the imager 10 once in each of a state in which the first grating G401, the second grating G402, and the third grating G403 are arranged on the X1 side (the state in FIG. 9) and a state in which the first grating G401, the second grating G402, and the third grating G403 are arranged on the X2 side (the state in FIG. 10) has been shown in the aforementioned second embodiment, the present invention is not limited to this. In the present invention, imaging may be performed a plurality of times in each of a state in which the first grating G401, the second grating G402, and the third grating G403 are arranged on the X1 side and a state in which the first grating G401, the second grating G402, and the third grating G403 are arranged on the X2 side. In this case, for example, as in an X-ray imaging apparatus 1000 shown in FIGS. 19 and 20, imaging may be performed a plurality of times by an imager 10 so as to change an angle of incidence of X-rays on a subject T to be imaged, and first images and second images may be generated in a first detection region R401 and a second detection region R402 in each imaging in which the angle of incidence is changed. In this case, for example, an image processor may be configured to select the first images and the second images having the same angles of incidence of X-rays on the subject T, and to generate a phase contrast image and an absorption image based on the selected first images and second images. Note that the X-ray imaging apparatus 1000 is a modified example of the second embodiment.

As shown in FIGS. 19 and 20, the X-ray imaging apparatus 1000 includes a moving mechanism 54, a moving mechanism 454, and a controller 1050. The moving mechanism 54 and the moving mechanism 454 are the same as the moving mechanisms provided in the X-ray imaging apparatus 100 and the X-ray imaging apparatus 400, respectively. The controller 1050 is configured to control the operation of the moving mechanism 54 and the moving mechanism 454. The controller 1050 includes an image processor 1050a.

The X-ray imaging apparatus 1000 is configured to perform imaging at a plurality of positions in an X direction while continuously changing the relative positions of the imager 10 and first, second, and third gratings G1, G2, and G3 in a predetermined direction (X direction) by the moving mechanism 54 in a state in which the first grating G401, the second grating G402, and the third grating G403 are arranged on the X2 side (a state in FIG. 19). The image processor 1050a is configured to generate a plurality of first images captured at the plurality of positions in the X direction (having different angles of incidence of X-rays on the subject T). Furthermore, the X-ray imaging apparatus 1000 is configured to perform imaging at the plurality of positions in the X direction while continuously changing the relative positions of the imager 10 and the first, second, and third gratings G1, G2, and G3 in the predetermined direction (X direction) by the moving mechanism 54 in a state in which the first grating G401, the second grating G402, and the third grating G403 are arranged on the X1 side (a state in FIG. 20). The image processor 1050a is configured to generate a plurality of second images captured at the plurality of positions in the X direction (having different angles of incidence of X-rays on the subject T).

With the configuration of the X-ray imaging apparatus 1000 described above, the image processor 1050a can generate the phase contrast image and the absorption image based on the first images and the second images having the same angles of incidence of X-rays on the subject T among the plurality of first images and the plurality of second images. Thus, the phase contrast image and the absorption image having the same angles of incidence of X-rays on the subject T can be generated, and thus the phase contrast image and the absorption image can be accurately compared even when the subject T is thick. In addition, the image processor 1050a can generate the phase contrast image and the absorption image by combining a plurality of images having different angles of incidence of X-rays on the subject T among the plurality of first images and the plurality of second images. Thus, the phase contrast image and the absorption image with improved resolution in a direction of incidence of X-rays on the subject T can be generated.

In the X-ray imaging apparatus 100 according to the first embodiment, the moving mechanism 54 is configured to change the relative positions of the first detection region R1 and the second detection region R2 with respect to the subject T by moving, in the X direction, the structures from the X-ray source 11 to the detector 12 aligned in the optical axis direction (Z direction). That is, imaging can be performed a plurality of times by the imager 10 so as to change an angle of incidence of the X-rays on the subject T, and the first images and the second images can be generated in the first detection region R1 and the second detection region R2 in each imaging in which the angle of incidence is changed. Therefore, similarly to the X-ray imaging apparatus 1000 according to the modified example of the second embodiment described above, the image processor may be configured to select the first images and the second images having the same angles of incidence of X-rays on the subject T, and to generate the phase contrast image and the absorption image based on the selected first images and second images as an modified example of the first embodiment.

DESCRIPTION OF REFERENCE NUMERALS

10: imager
11: X-ray source
12, 812, 912: detector
12a: detection surface (of a detector)
31, 231, 331: collimator (irradiation range adjustment member)
31a, 331a: collimator hole (first irradiation range adjuster)
31b, 231b: collimator hole (second irradiation range adjuster)
41a: filter (first filter)
41b: filter (second filter)
50a, 250a, 350a, 450a, 550a, 1050a: image processor
54, 454, 954: moving mechanism (relative position changer)
71, 471: phase contrast image (phase or scattering contrast image)
71a, 471a, 471b, 571a, 571b: first image
72, 472: absorption image
72a, 472a, 472b, 572a, 572b: second image
80, 580: scattered-ray grid (anti-scatter member)
100, 200, 300, 400, 500, 600, 700, 800, 900, 1000: X-ray imaging apparatus
G1, G301, G401, G501: first grating
G2, G302, G402, G502: second grating
R1, R401, R501: first detection region
R2, R402, R502, R802, R902: second detection region
T: subject

The invention claimed is:

1. An X-ray imaging apparatus comprising:
an X-ray source;
a first grating having a grating pattern formed to diffract or shield X-rays radiated from the X-ray source;
a detector including a first detection region configured to detect the X-rays that have passed through the first grating and have reached the first detection region, and a second detection region configured to detect the X-rays that have reached the second detection region without passing through the first grating;
a relative position changer configured to change relative positions of the first detection region and the second detection region with respect to a subject to be imaged; and
an image processor configured to generate a phase or scattering contrast image based on a plurality of first images acquired by the first detection region at a plurality of relative positions of the first detection region with respect to the subject, and to generate an absorption image based on a plurality of second images acquired by the second detection region at a plurality of relative positions of the second detection region with respect to the subject.

2. The X-ray imaging apparatus according to claim 1, wherein the image processor is configured to generate a dark-field image based on the plurality of first images acquired by the first detection region at the plurality of relative positions of the first detection region with respect to the subject, and to generate the absorption image based on the plurality of second images acquired by the second detection region at the plurality of relative positions of the second detection region with respect to the subject.

3. The X-ray imaging apparatus according to claim 1, wherein the relative position changer includes a moving mechanism configured to change the relative positions of the first detection region and the second detection region with respect to the subject by;
moving an imager including the X-ray source and the detector and the first grating with respect to the subject;
moving the subject with respect to the imager and the first grating; or
moving the first grating with respect to the subject and the imager.

4. The X-ray imaging apparatus according to claim 3, wherein the moving mechanism is configured to continuously change relative positions of the imager and the first grating with respect to the subject in a predetermined direction by continuously moving either the imager and the first grating or the subject in the predetermined direction in a state in which a relative position of the first grating with respect to the imager is maintained; and
the image processor is configured to generate the phase or scattering contrast image and the absorption image based on the plurality of first images and the plurality of second images, respectively, generated by continuous changes of the relative positions of the imager and the first grating with respect to the subject by the moving mechanism.

5. The X-ray imaging apparatus according to claim 4, wherein the first detection region and the second detection region are aligned along a direction in which the relative positions of the imager and the first grating with respect to the subject are continuously changed; and
the moving mechanism is configured to change the relative positions in such a manner that the detector detects the X-rays from a side of the second detection region among the first detection region and the second detection region.

6. The X-ray imaging apparatus according to claim 4, further comprising an irradiation range adjustment member arranged on a side of the X-ray source with respect to the subject between the X-ray source and the first grating, the irradiation range adjustment member including a first irradiation range adjuster configured to adjust an irradiation range of the X-rays reaching the first detection region and a second irradiation range adjuster configured to adjust an irradiation range of the X-rays reaching the second detection region.

7. The X-ray imaging apparatus according to claim 6, wherein the first irradiation range adjuster and the second irradiation range adjuster are arranged apart from each other along a direction in which the relative positions of the imager and the first grating with respect to the subject are continuously changed.

8. The X-ray imaging apparatus according to claim 6, wherein the irradiation range of the X-rays reaching the second detection region adjusted by the second irradiation range adjuster is smaller than the irradiation range of the X-rays reaching the first detection region adjusted by the first irradiation range adjuster.

9. The X-ray imaging apparatus according to claim 6, wherein at least the second irradiation range adjuster of the first irradiation range adjuster and the second irradiation range adjuster includes a plurality of second irradiation range adjusters; and
the plurality of second irradiation range adjusters are configured to adjust the irradiation range of the X-rays reaching the second detection region by changing a number of the second irradiation range adjusters that transmit the X-rays.

10. The X-ray imaging apparatus according to claim 1, further comprising a first filter arranged on a side of the X-ray source with respect to the subject and configured to adjust a spectrum of the X-rays reaching the first detection region, and a second filter arranged on the side of the X-ray source with respect to the subject and configured to adjust a spectrum of the X-rays reaching the second detection region.

11. The X-ray imaging apparatus according to claim 10, further comprising an adjustment mechanism configured to adjust a relative position between the first grating and the first filter and a relative position between the first grating and the second filter.

12. The X-ray imaging apparatus according to claim 3, wherein the moving mechanism is configured to change the relative positions of the first detection region and the second detection region with respect to the subject by moving the first grating with respect to the subject and the imager; and
    the imager is configured to perform imaging a plurality of times, and generate the first images and the second images in a state in which the relative positions of the first detection region and the second detection region with respect to the subject are changed by the moving mechanism such that the relative positions are different in each imaging.

13. The X-ray imaging apparatus according to claim 12, wherein the first detection region and the second detection region respectively include a plurality of first detection regions and a plurality of second detection regions, and are alternately arranged.

14. The X-ray imaging apparatus according to claim 12, further comprising an anti-scatter member arranged at a position corresponding to the second detection region among the first detection region and the second detection region in a vicinity of a detection surface of the detector and configured to remove scattered rays.

15. The X-ray imaging apparatus according to claim 3, wherein a distance of the second detection region from the subject is smaller than a distance of the first detection region from the subject.

16. The X-ray imaging apparatus according to claim 3, wherein imaging is performed a plurality of times so as to change an angle of incidence of the X-rays on the subject, and the first images and the second images are generated in the first detection region and the second detection region in each imaging in which the angle of incidence is changed; and
    the image processor is configured to select the first images and the second images having same angles of incidence of the X-rays on the subject, and to generate the phase or scattering contrast image and the absorption image based on the first images and second images that have been selected.

17. The X-ray imaging apparatus according to claim 1, further comprising a second grating arranged between the first grating and the detector and configured to interfere with a self-image of the first grating.

18. The X-ray imaging apparatus according to claim 1, wherein a resolution of an image to be detected by the first detection region is different from a resolution of an image to be detected by the second detection region.

19. The X-ray imaging apparatus according to claim 1, wherein the detector includes a scintillator configured to detect the X-rays and emits fluorescence, and a photodetector configured to detect the fluorescence; and
    the scintillator has a different structure between a portion corresponding to the first detection region and a portion corresponding to the second detection region.

\* \* \* \* \*